(12) United States Patent
Johs et al.

(10) Patent No.: US 7,746,472 B1
(45) Date of Patent: Jun. 29, 2010

(54) AUTOMATED ELLIPSOMETER AND THE LIKE SYSTEMS

(75) Inventors: Blaine D. Johs, Lincoln, NE (US); Ping He, Lincoln, NE (US); Martin M. Liphardt, Lincoln, NE (US); Christopher A. Goeden, Lincoln, NE (US); John A. Woollam, Lincoln, NE (US); James D. Welch, Omaha, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 187 days.

(21) Appl. No.: 12/231,074

(22) Filed: Aug. 29, 2008

Related U.S. Application Data

(63) Continuation-in-part of application No. 11/408,679, filed on Apr. 21, 2006, now Pat. No. 7,505,134, and a continuation-in-part of application No. 11/105,852, filed on Apr. 14, 2005, now Pat. No. 7,277,171, and a continuation-in-part of application No. 10/829,620, filed on Apr. 22, 2004, now Pat. No. 7,193,710, and a continuation-in-part of application No. 10/925,333, filed on Aug. 24, 2004, now Pat. No. 7,265,838, and a continuation-in-part of application No. 10/050,802, filed on Jan. 15, 2002, now Pat. No. 6,859,278, application No. 12/231,074, and a continuation-in-part of application No. 10/699,540, filed on Nov. 1, 2003, now Pat. No. 7,158,231, and a continuation-in-part of application No. 10/857,774, filed on May 28, 2004, now Pat. No. 7,274,450.

(60) Provisional application No. 60/676,664, filed on Apr. 30, 2005, provisional application No. 60/261,243, filed on Jan. 16, 2001, provisional application No. 60/263,874, filed on Jan. 25, 2001, provisional application No. 60/287,784, filed on May 2, 2001, provisional application No. 60/564,747, filed on Apr. 23, 2004, provisional application No. 60/480,851, filed on Jun. 24, 2003, provisional application No. 60/580,314, filed on Jun. 17, 2004, provisional application No. 60/424,589, filed on Nov. 7, 2002, provisional application No. 60/427,043, filed on Nov. 18, 2002.

(51) Int. Cl.
 *G01J 4/00* (2006.01)
(52) U.S. Cl. .................................... 356/369; 356/399
(58) Field of Classification Search .......... 356/364–369, 356/399–401; 250/225
 See application file for complete search history.

(56) References Cited

U.S. PATENT DOCUMENTS

| | | | |
|---|---|---|---|
| 3,874,797 A | 4/1975 | Kasai | 356/369 |
| 4,053,232 A | 10/1977 | Dill | 356/118 |
| 4,647,207 A | 3/1987 | Bjork et al. | 356/369 |
| 4,668,086 A | 5/1987 | Rosencwaig et al. | 356/33 |
| 4,672,196 A | 6/1987 | Canino | 250/225 |
| 5,229,833 A | 7/1993 | Stewart | 356/364 |
| 5,329,357 A | 7/1994 | Bernoux et al. | 356/369 |
| 5,343,293 A | 8/1994 | Berger et al. | 356/369 |
| 5,410,409 A | 4/1995 | Ray | 356/369 |
| 5,412,473 A | 5/1995 | Rosencwaig et al. | 356/451 |
| 5,504,582 A | 4/1996 | Johs et al. | 356/369 |

(Continued)

*Primary Examiner*—Hoa Q Pham
(74) *Attorney, Agent, or Firm*—James D. Welch

(57) ABSTRACT

Systems and methodology for orienting the tip/tilt and vertical height of samples, preferably automated, as applied in ellipsometer and the like systems.

29 Claims, 14 Drawing Sheets

U.S. PATENT DOCUMENTS

| | | | |
|---|---|---|---|
| 5,521,706 A | 5/1996 | Green et al. | 356/369 |
| 5,581,350 A | 12/1996 | Chen et al. | 356/369 |
| 5,582,646 A | 12/1996 | Woollam et al. | 118/708 |
| 5,596,406 A | 1/1997 | Rosencwaig et al. | 356/327 |
| 5,666,201 A | 9/1997 | Johs et al. | 356/369 |
| 5,706,087 A | 1/1998 | Thompson | 356/364 |
| 5,706,212 A | 1/1998 | Thompson et al. | 356/367 |
| 5,757,494 A | 5/1998 | Green et al. | 356/369 |
| 5,764,365 A | 6/1998 | Finarov | 356/630 |
| 5,872,630 A | 2/1999 | Johs et al. | 356/359 |
| 5,963,327 A | 10/1999 | He | 356/369 |
| 6,034,777 A | 3/2000 | Johs et al. | 356/369 |
| 6,081,334 A | 6/2000 | Grimbergen et al. | 356/499 |
| 6,744,510 B2 * | 6/2004 | Gweon et al. | 356/369 |
| 7,084,978 B1 * | 8/2006 | Liphardt | 356/364 |
| 7,136,162 B1 * | 11/2006 | Liphardt et al. | 356/369 |
| 7,136,172 B1 * | 11/2006 | Johs et al. | 356/614 |
| 7,327,456 B1 * | 2/2008 | Woollam et al. | 356/364 |
| 7,333,198 B1 * | 2/2008 | Liphardt | 356/364 |
| 7,505,134 B1 * | 3/2009 | Johs et al. | 356/369 |
| 2009/0103093 A1 * | 4/2009 | Liphardt et al. | 356/369 |
| 2009/0103094 A1 * | 4/2009 | Hilfiker et al. | 356/369 |

* cited by examiner

AUTOMATED ELLIPSOMETER AND THE LIKE SYSTEMS

This Application is a CIP of application Ser. No. 11/408,679 Filed Apr. 21, 2006, now U.S. Pat. No. 7,505,134, and therevia Claims benefit of Provisional Application 50/676,664 Filed Apr. 30, 2005. This Application is further a Continuation-In-Part of Utility application Ser. Nos. 11/105,852 Filed Apr. 14, 2005, now U.S. Pat. No. 7,277,171; Ser. No. 10/829,620 Filed Apr. 22, 2004, now U.S. Pat. No. 7,193,710; and of 10/925,333 Filed Aug. 24, 2004, now U.S. Pat. No. 7,265,838, and therevia of 10/050,802 Filed Jan. 15, 2002, (now U.S. Pat. No. 6,859,278). Via the above Applications this Application Claims Benefit of Provisional Application Ser. Nos. 60/261,243 Filed Jan. 16, 2001, 60/263,874 Filed Jan. 25, 2001, and 60/287,784 Filed May 2, 2001. This Application is further a CIP of application Ser. No. 10/699,540 Filed Nov. 1, 2003, now U.S. Pat. No. 7,158,231, and Ser. No. 10/857,774 Filed May 28, 2004, now U.S. Pat. No. 7,274,450. Via the above Applications the present Application Claims benefit of Provisional Applications 60/564,747 Filed Apr. 23, 2004, 60/580,314 Filed Jun. 17, 2004, 60/424,589 Filed Nov. 7, 2002, 60/427,043 Filed Nov. 18, 2002, and 60/480,851 Filed Jun. 24, 2003.

TECHNICAL FIELD

The present invention relates to ellipsometry, and more particularly to a system and method for aligning a sample tip/tilt orientation and height, so that a beam of electromagnetic radiation approaches a surface thereof at a known angle and plane of incidence, reflects therefrom and enters a data detector.

BACKGROUND

To begin, it is first disclosed that it is known to place samples on stages in ellipsometer and the like systems, and to cause a polarized beam of electromagnetic radiation to impinge on said sample at an oblique angle thereto, interact with said sample and then enter a detector. It is also known that the "tilt" of a sample surface at a specific location thereon can affect realized angle and plane of incidence values actually achieved. Further, it is known to adjust the vertical height of the stage to position a sample such that a beam of electromagnetic radiation reflecting therefrom enters a detector.

Continuing, spectrophotometer, reflectometer, polarimeter, ellipsometer and the like systems are known, (eg. Rotating Analyzer, Rotating Polarizer, Rotating Compensator, Modulator Element Ellipsometer), and the like systems (SYS) are known. Typical construction provides of such systems include a Sample Supporting Stage which is substantially fixed in location. Functionally oriented with respect thereto are a Substantially Fixed Position Source Means (S) for providing a beam of electromagnetic radiation at an oblique angle to said Sample Supporting Stage, and a Substantially Fixed Position Data Detector Means (D) for intercepting Electromagnetic Radiation which Reflects (or Transmittes through), a Sample placed on said Sample Supporting Stage. Typical procedure is to place a Sample onto the Sample Supporting Stage, cause a beam of Electromagnetic Radiation to impinge thereonto, and record data produced by the Data Detector Means in response to electromagnetic radiation which enters thereinto, which data is analyzed to provide insight into Sample Optical and Physical properties. Said procedure can include adjustment of the Sample Supporting Stage in an "X"-"Y" Plane, and along a "Z" direction perpendicular to its surface, (ie. a vertical position adjustment where the Electromagnetic Radiation approaches the Sample at an oblique angle from a laterally located Source). This purpose of said adjustment is to, for instance, enable the directing of a beam of Electromagnetic Radiation Reflected from a Sample placed on said Sample Supporting Stage into the Data Detector without moving the Data Detector so it intercepts a beam exiting said Sample. It should be appreciated then that conventional Reflectometer, Spectrophotometer, Ellipsometer and Polarimeter Systems which include provision for such Sample positioning adjustment and orientation with respect to an impinging Electromagnetic beam, typically do so by allowing the Sample Supporting Stage position to be adjusted, rather than by effecting simultaneous change in location of the Source and Data Detector with respect to the Sample Supporting Stage, because it is far simpler to implement Sample Supporting Stage location change.

Continuing, a typical goal in ellipsometry is to obtain, for each wavelength in, and angle of incidence of said beam of electromagnetic radiation caused to interact with a sample system, sample system characterizing PSI and DELTA values, (where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$, caused by interaction with said sample system:

$$\mathrm{TAN}(\psi)e^{(i\Delta)} = r_p/r_s$$

As indicated above, Ellipsometer Systems generally include a source of a beam of electromagnetic radiation, a Polarizer, which serves to impose a known, (typically linear), state of polarization on a beam of electromagnetic radiation, a Stage for supporting a sample system, and an Analyzer which serves to select a polarization state in a beam of electromagnetic radiation after it has interacted with a material system, and pass it to a Detector System for analysis therein. As well, one or more Compensator(s) can be present and serve to affect a phase retardence between orthogonal components of a polarized beam of electromagnetic radiation. A number of types of ellipsometer systems exist, such as those which include rotating elements and those which include modulation elements. Those including rotating elements include Rotating Polarizer (RP), Rotating Analyzer (RA) and Rotating Compensator (RC). A preferred embodiment is a Rotating Compensator Ellipsometer System because they do not demonstrate "Dead-Spots" where obtaining ellipsometric data is difficult. They can read PSI and DELTA of a Material System over a full Range of Degrees with the only limitation being that if PSI becomes essentially zero (0.0), one can't then determine DELTA as there is not sufficient PSI Polar Vector Length to form the angle between the PSI Vector and an "X" axis. In comparison, Rotating Analyzer and Rotating Polarizer Ellipsometers have "Dead Spots" at DELTA's near 0.0 or 180 Degrees and Modulation Element Ellipsometers also have a "Dead Spot" at PSI near 45 Degrees). The utility of Rotating Compensator Ellipsometer Systems should then be apparent. Another benefit provided by Rotating Compensator Ellipsometer Systems is that the Polarizer (P) and Analyzer (A) positions are fixed, and that provides benefit in that polarization state sensitivity to input and output optics during data acquisition is essentially non-existent. This enables relatively easy use of optic fibers, mirrors, lenses etc. for input/output.

While Data taken at one (AOI) and one or multiple wavelengths is often sufficient to allow ellipsometric characterization of a sample system, the results of Ellipsometric Investigation can be greatly enhanced by using multiple (AOI's) to obtain additional data sets. However, while it is relatively easy to provide Wavelength change without extensive difficult physical Ellipsometer System Orientation change, it is typically difficult to change the Angle-of-Incidence (AOI) that a Beam of Electromagnetic Radiation makes to a surface of a sample system. An (AOI) change requires that both the Source of the Electromagnetic Beam and the Detector must be re-positioned and aligned, and such is tedious and time consuming.

While present invention systems can be applied in any material system investigation system such as Polarimeter, Reflectometer, Spectrophotometer and the like Systems, an important application is in Ellipsometer Systems, whether monochromatic or spectroscopic. It should therefore be understood that Ellipsometry involves acquisition of sample system characterizing data at single or multiple Wavelengths, and at one or more Angle(s)-of-Incidence (AOI) of a Beam of Electromagnetic Radiation to a surface of the sample system. Ellipsometry is generally well described in a great many number of publications, one such publication being a review paper by Collins, titled "Automatic Rotating Element Ellipsometers: Calibration, Operation and Real-Time Applications", Rev. Sci. Instrum. 61(8) (1990).

It is also noted that Ultraviolet (UV) or Infra-Red (IR) Wavelengths are absorbed by oxygen or water vapor, hence where they are applied, it is necessary to evacuate or purge at least the region around a sample.

Further, it is to be understood that causing a polarized beam of electromagnetic radiation to interact with a sample system generally causes change in the ratio of the intensities of orthogonal components thereof and/or the phase shift between said orthogonal components. The same is generally true for interaction between any system component and a polarized beam of electromagnetic radiation. In recognition of the need to isolate the effects of an investigated sample system from those caused by interaction between a beam of electromagnetic radiation and system components other than said sample system, (to enable accurate characterization of a sample system per se.), this Specification incorporates by reference the regression procedure of U.S. Pat. No. 5,872,630 in that it describes simultaneous evaluation of sample characterizing parameters such as PSI and DELTA, as well system characterizing parameters, and this Specification also incorporates by reference the Vacuum Chamber Window Correction methodology of U.S. Pat. No. 6,034,777 to account for phase shifts entered between orthogonal components of a beam of electromagnetic radiation, by present invention system multiangle prisms and/or lenses.

Another Patent which is incorporated hereinto by reference is U.S. Pat. No. 5,969,818 to Johs et al. Said 818 Patent describes a Beam Folding Optics System which serves to direct an electromagnetic beam via multiple reflections, without significantly changing the phase angle between orthogonal components therein. Briefly, two pairs of mirrors are oriented to form two orthogonally related planes such that the phase shift entered to an electromagnetic beam by interaction with the first pair of mirrors is canceled by interaction with the second pair.

Another Patents incorporated hereinto by reference is U.S. Pat. No. 5,757,494 to Green et al., in which is taught a method for extending the range of Rotating Analyzer/Polarizer ellipsometer systems to allow measurement of DELTA'S near zero (0.0) and one-hundred-eighty (180) degrees. Said Patent describes the presence of a window-like variable bi-refringent component which is added to a Rotating Analyzer/Polarizer ellipsometer system, and the application thereof during data acquisition, to enable the identified capability.

A Patent to Thompson et al. U.S. Pat. No. 5,706,212 teaches a mathematical regression based double Fourier series ellipsometer calibration procedure for application, primarily, in calibrating ellipsometers system utilized in infrared wavelength range. Bi-refringent window-like compensators are described as present in the system thereof, and discussion of correlation of retardations entered by sequentially adjacent elements which do not rotate with respect to one another during data acquisition is described therein.

A Patent to Woollam et al, U.S. Pat. No. 5,582,646 is disclosed as it describes obtaining ellipsometric data through windows in a vacuum chamber, utilizing other than a Brewster Angle of Incidence.

Patent to Woollam et al, U.S. Pat. No. 5,373,359, Patent to Johs et al. U.S. Pat. No. 5,666,201 and Patent to Green et al., U.S. Pat. No. 5,521,706, and Patent to Johs et al., U.S. Pat. No. 5,504,582 are disclosed for general information as they pertain to Rotating Analyzer ellipsometer systems.

Patent to Bernoux et al., U.S. Pat. No. 5,329,357 is identified as it describes the use of optical fibers as input and output means in an ellipsometer system.

A Patent to Finarov, U.S. Pat. No. 5,764,365 is disclosed as it describes a system for moving an ellipsometer beam over a large two-dimensional area on the surface of a sample system, which system utilizes beam deflectors.

A Patent to Berger et al., U.S. Pat. No. 5,343,293 describes an Ellipsometer which comprises prisms to direct an electromagnetic beam onto a sample system.

A Patent to Canino, U.S. Pat. No. 4,672,196 describes a system which allows rotating a sample system to control the angle of incidence of a beam of electromagnetic radiation thereonto. Multiple detectors are present to receive the resulting reflected beams.

A Patent to Bjork et al., U.S. Pat. No. 4,647,207 describes an ellipsometer system in which reflecting elements are moved into the path of a beam of electromagnetic radiation.

U.S. Pat. No. 6,081,334 to Grimbergen et al. describes a system for detecting semiconductor end point etching including a means for scanning a beam across the surface of a substrate.

A Patent to Ray, U.S. Pat. No. 5,410,409 describes a system for scanning a laser beam across a sample surface.

U.S. Pat. No. 3,874,797 to Kasai describes means for directing a beam of electromagnetic radiation onto the surface of a sample using totally internally reflecting prisms.

U.S. Pat. No. 5,412,473 to Rosencwaig et al., describes a ellipsometer system which simultaneously provides an electromagnetic beam at a sample surface at numerous angles of incidence thereto.

A Patent to Chen et al., U.S. Pat. No. 5,581,350 is identified as it describes the application of regression in calibration of ellipsometer systems.

Existing Provisional and Utility Applications, (ie. 60/459,690 filed Apr. 3, 2003 and Ser. No. 10/652,696 filed Sep. 2, 2003), by the Inventor herein, show a prior art system for detecting sample tilt, and a system which utilizes an ellipsometer beam reflected from a sample to perform vertical positioning of a stage. A beam splitter is used to divert a portion of the reflected beam into a detector and used to mediate adjustment of the sample's vertical position and/or tilt. While said system does not "lock-in" tilt and relative position of the ellipsometer and sample, it provides for aligning a sample system and controlling the angle and plane of incidence at which a beam of electromagnetic radiation obliquely impinges on a monitored location of a surface of a sample, and comprises, as viewed in side elevation:

a sample supporting stage which can be translated in "X", "Y" or "Z" directions as well as rotated about "X", "Y" and optionally "Z" axes;

vertically above said stage there being a first beam splitter means, a lens and a first camera means for providing a view of a portion of the surface of said sample, said first beam splitter means optionally having positioned on a lower surface thereof light emitting means for providing light to the surface of said sample;

laterally with respect to said first beam splitter means there being a reflection means;

vertically above said reflection means there being a second beam splitter;

vertically above said second beam splitter there being a second camera means and laterally with respect to said second beam splitter, there being sequentially a lens and an essentially point source of electromagnetic radiation;

said first and second camera means each having associated therewith display means.

Said system further comprises an ellipsometer polarization state generator to cause, and a polarization stage detector to monitor, a beam of electromagnetic radiation which in use impinges on said monitored location on said surface of said sample at an oblique angle thereto.

In use said first camera means and its associated display means provide a view of at least a portion of the surface of a sample utilizing light provided by said light emitting means for providing light to the surface of said sample positioned on said lower surface of said first beam splitter, and said essentially point source of electromagnetic radiation provides electromagnetic radiation to the surface of said sample via said second beam splitter, said reflective means and said first beam splitter, and said sample supporting stage is caused to be translated in any of said "X", "Y" and "Z" directions as well as rotated about said "X", "Y" and optionally "Z" axes which are necessary to cause an interrogating beam of electromagnetic radiation provided by said essentially point source of a source of electromagnetic radiation to reflect from the surface of said sample, proceed back through said first beam splitter means, reflect from said reflective means, pass through said second beam splitter means, enter said second camera means and cause an image on the display means associated therewith which indicates that the monitored location on the sample surface is oriented so as to face substantially vertically.

The purpose of the foregoing is to align said sample surface to assure that said beam of electromagnetic radiation provided to said monitored location on the surface of said sample at an oblique angle approaches said surface at known intended angle of incidence and plane of incidence orientation, rather than at an angle of incidence and plane of incidence orientation which is modified by surface irregularities or non-flat samples.

Said system can further comprise a polarizer means in the path of said beam of electromagnetic radiation provided by said essentially point source of electromagnetic radiation, and in which said first beam splitter is sensitive to polarization state, and the polarizer means can be adjustable to enable control of the direction of polarization. The system point source of a source of electromagnetic radiation can comprise a fiber optic.

A Patent to Abraham et al., U.S. Pat. No. 6,091,499 describes a method and system for automatic relative adjustment of samples in relation to an ellipsometer. Paraphrasing, said Abraham et al. system basically comprises:

a system for orienting a sample on a stage in an ellipsometer system comprising a first light source, a polarizer, said stage, an analyzer and a detector;

said system further comprising a detection system having a second light source, wherein said detection system is independently adjustable in relation to said ellipsometer, and wherein said detection system can be electronically locked into position relative to said ellipsometer so that said ellipsometer and said detection system can be adjusted as one unit in relationship to said stage, wherein said detection system can detect both a tilt of a sample placed onto said stage, and a distance of said sample from a coordinate source of the ellipsometer in two perpendicular axes; and said system further comprising an adjusting device, wherein said adjusting device can adjust tilt of said stage, and wherein said adjusting device can adjust the position of said ellipsometer and detection system when in an electronically locked relationship with respect to one another.

Additional known Patents are:

Patent to Coates U.S. Pat. No. 4,373,817;
Patent to Coates U.S. Pat. No. 5,045,704;
RE. 34,783 to Coates;
Patent to Mikkelsen et al., U.S. Pat. No. 6,600,560;
Patent to Fanton et al., U.S. Pat. No. 5,596,411;
Patent to Piwonka-Corle et al., U.S. Pat. No. 5,910,842;
Patent to Piwonka-Corle et al., U.S. Pat. No. 5,608,526;
Patent to Bareket, U.S. Pat. No. 5,889,593;
Patent to Norton et al., U.S. Pat. No. 5,486,701;
Patent to Aspnes et al., U.S. Pat. No. 5,900,939;
PCT Application Publication WO 99/45340;
Published Application of Stehle et al., No. US2002/0024668 A1.

While the above Patents describe various methodology, none disclose a method of aligning an ellipsometer system which comprises:

an ellipsometer source of a beam of electromagnetic radiation;

a stage for supporting a sample and having means for effecting tip/tilt and translation thereof;

a data detector of electromagnetic radiation;

and which method comprises:

a) placing an alignment sample on said stage;

b) generally orienting said ellipsometer source of a beam of electromagnetic radiation so that it directs a beam of electromagnetic radiation onto a first location of said alignment sample at an oblique angle, which beam then reflects from said alignment sample and enters said data detector so that it provides an output signal;

itteratively repeating steps in any functional order until the output of the data or alignment detector is substantially the same when the stage is caused to effect translation of said alignment sample so that said beam is directed to a second or third or fourth location thereon at said oblique angle, reflects therefrom and enters said data detector, followed by adjusting the tip/tilt of said stage with the result being that the stage is oriented in tip/tilt so that no matter from what location on said alignment sample said beam is caused to reflect, the output from said data detector remains substantially the same;

said method then optionally further comprising:

d) while monitoring the data detector or alignment output signal moving the location and orientation thereof until said output signal therefrom is substantially maximized.

Need remains for additional systems and methods for orienting the vertical position, and tilt, of samples in ellipsometer, polarimeter, spectrophotometer and the like systems.

DISCLOSURE OF THE INVENTION

Present Invention System

A present invention system can comprise:
source of a beam of spectroscopic electromagnetic radiation;
stage for supporting a sample;
data detector of spectroscopic electromagnetic radiation; and
between said source and stage, means for receiving a beam of spectroscopic electromagnetic radiation from said source thereof and providing it to a surface of a sample on said stage at any of at least two angles-of-incidence with respect to said surface, with at least one of said angles-of-incidence being available as a focused, and as a non-focused, beam onto said sample surface.

Said source of a beam of spectroscopic electromagnetic radiation, data detector of spectroscopic electromagnetic radiation, and means for receiving a beam of spectroscopic electromagnetic radiation from said source thereof and providing it to a surface of a sample on said stage at any of at least two angles-of-incidence with respect to said surface, are functionally mounted so as to enable movement as a unit.

Said system further comprises means for detecting the direction in which a normal to a sample surface projects and means for detecting the angle and plane of incidence of a beam of electromagnetic radiation provided by said source of a beam of spectroscopic electromagnetic radiation, and providing signals which are representative thereof.

Said system further comprises actuator means for receiving said representative signals and in response automatically controlling the separation between:
  as a unit, said source, data detector, and means for receiving a beam of spectroscopic electromagnetic radiation from said source thereof and providing it to a sample on said stage; and
  the surface of a sample on said stage; and
  actuator means for receiving said representative signals and in response automatically controlling the effective tip/tilt between said beam of electromagnetic radiation provided by said source of a beam of spectroscopic electromagnetic radiation with respect to said sample surface, and therefor the orientation of the angle and plane of incidence of said spectroscopic beam of electromagnetic radiation provided by said source of a beam of spectroscopic electromagnetic radiation with respect to said sample surface.

Optionally, said system can comprise means for causing rotation of said sample about a normal to said surface thereof.

Said system can further comprise between said stage and detector, means for receiving a beam of spectroscopic electromagnetic radiation reflected from said sample and providing it to said detector in any of at least two angles-of-incidence with respect to said surface, with at least one of said angles-of-incidence being available as a focused, and as a non-focused, beam onto said sample surface.

Said system can further comprise a polarizer between said source of a beam of spectroscopic electromagnetic radiation said stage, and an analyzer between said stage and said detector, and in which said system is an ellipsometer or polarimeter.

It is noted that actuator action can be arranged to causes a normal to the sample surface at the point at which said beam of spectroscopic electromagnetic radiation impinges, to project substantially vertically upward in laboratory coordinates.

Another recitation of a present invention system provides that it comprise:
  a source of a beam of spectroscopic electromagnetic radiiation;
  a stage for supporting a sample;
  a data detector of spectroscopic electromagnetic radiation; and
  between said source and stage, means for receiving a beam of spectroscopic electromagnetic radiation from said source thereof and providing it to the surface of a sample on said stage at any of at least two angles-of-incidence with respect to said surface, with at least one of said angles-of-incidence being available as a focused, and as a non-focused, beam onto said sample surface.

Said system is characterized by at least one selection from the group consisting of:
  said stage for supporting said sample comprises means for moving said sample in two orthogonal directions in a plane substantially parallel to said sample surface and/or in a direction substantially perpendicular thereto; and
  the presence of means for moving, as a group,
    said source;
    data detector; and
    means for receiving a beam of spectroscopic electromagnetic radiation from said source thereof and providing it to a sample on said stage;
  in two orthogonal directions in a plane substantially parallel to said sample surface and/or in a direction substantially perpendicular thereto.

Said system can further comprising:
  means for controlling stage tip/tilt and therefor the orientation of the plane in which said sample surface is present; and
  means for causing rotation of said sample.

The stage for supporting a sample in said system can comprise two sections:
  the first section being comprised of means for adjusting a sample location in two dimensions substantially parallel to the surface of said sample, and
  the second section being comprised of means for moving the first section in a direction to place said first section closer to or further away from said source, data detector and said means for receiving a beam of spectroscopic electromagnetic radiation from said source thereof and providing it to a sample on said stage, and for adjusting tip/tilt of the surface of said sample.

In use the first section of said stage can be applied to position a spot on a surface of a sample placed on said stage in a plane which is parallel to that of a plane formed by the two dimensions in which said first section can cause movement. The second section of said stage can be applied to orient said surface of a sample placed on the first section with respect to a beam of spectroscopic electromagnetic radiation provided by said source thereof via adjustment of the location of a surface of a sample along a direction generally perpendicular to said sample surface, and to control the tip/tilt orientation of the plane in which said first section of said stage causes movement of said sample. The plane in which the first section causes the surface of a sample to move with respect to an electromagnetic beam from said source thereof can thus orient the plane of incidence, which includes both a perpendicular to the sample surface and the locus of said spectroscopic electromagnetic, so that both project substantially perpendicular to the sample surface.

Again, said system can further comprise a polarizer between said source of electromagnetic radiation and said stage, and an analyzer between said stage and said data detector and in which said system is an ellipsometer or polarimeter.

Said system can further comprise means for providing an alignment beam of electromagnetic radiation provided by said source of a beam of spectroscopic electromagnetic radiation or an alternative source, and an alignment detector, said alignment detector being positioned to detect when said sample is oriented so that said alignment beam approaches said sample surface so that, at the point of reflection therefrom, it reflects directly back along its incident locus, the purpose being to enable align said sample surface in a known orientation.

Said system can further comprise, between said stage and detector, means for receiving a beam of spectroscopic electromagnetic radiation reflected from said sample and providing it to said detector in any of at least two angles-of-incidence with respect to said surface, with at least one of said angles-of-incidence being available as a focused, and as a non-focused, beam onto said sample surface.

It is noted that any present invention system can further comprise a beam modulator which modulates at least one selection from the group consisting of:

said spectroscopic electromagnetic beam; and said alignment beam;

to distinguish said at least one selection from external light, thereby enabling use in rooms illuminated by non-modulated light.

Another present invention system comprises: source of a beam of spectroscopic electromagnetic radiation;

stage for supporting a sample;

data detector of spectroscopic electromagnetic radiation;

said system further comprising, between said source and stage, means for receiving a beam of spectroscopic electromagnetic radiation from said source thereof and providing it to a surface of a sample on said stage at any of at least two angles-of-incidence with respect to said surface, with at least one of said angles-of-incidence being available as a focused, and as a non-focused, beam onto said sample surface;

said source of a beam of spectroscopic electromagnetic radiation, data detector of spectroscopic electromagnetic radiation, and means for receiving a beam of spectroscopic electromagnetic radiation from said source thereof and providing it to a surface of a sample on said stage at any of at least two angles-of-incidence with respect to said surface, being functionally mounted so as to enable movement as a unit;

said system further comprising means for detecting the direction in which a normal to a sample surface projects and means for detecting the angle and plane of incidence of a beam of electromagnetic radiation provided by said source of a beam of spectroscopic electromagnetic radiation, and providing signals which are representative thereof;

said system further comprising actuator means for receiving said representative signals and in response automatically controlling the separation between:

as a unit, said source, data detector, and means for receiving a beam of spectroscopic electromagnetic radiation from said source thereof and providing it to a sample on said stage; and the surface of a sample on said stage;

said system further comprising actuator means for receiving said representative signals and in response automatically controlling the effective tip/tilt between said beam of electromagnetic radiation provided by said source of a beam of spectroscopic electromagnetic radiation with respect to said sample surface, and therefor the orientation of the angle and plane of incidence of said spectroscopic beam of electromagnetic radiation provided by said source of a beam of spectroscopic electromagnetic radiation with respect to said sample surface; and optionally, means for causing rotation of said sample about a normal to said surface thereof.

Said system can further comprise, between said stage and detector, means for receiving a beam of spectroscopic electromagnetic radiation reflected from said sample and providing it to said detector in any of at least two angles-of-incidence with respect to said surface, with at least one of said angles-of-incidence being available as a focused, and as a non-focused, beam onto said sample surface.

Said system can further comprise a polarizer between said source of a beam of spectroscopic electromagnetic radiation said stage, and an analyzer between said stage and said detector, and in which said system is an ellipsometer or polarimeter.

Said system can provide that the actuator action causes a normal to the sample surface at the point at which said beam of spectroscopic electromagnetic radiation impinges, to project substantially vertically upward in laboratory coordinates.

Present Invention Methodology

Continuing, a present invention method of aligning an ellipsometer system comprises providing an ellipsometer source of a beam of electromagnetic radiation, a stage for supporting a sample and having means for effecting tip/tilt and translation thereof, and a data detector of electromagnetic radiation. Said method then further comprises:

a) placing an alignment sample on said stage, where said alignment sample is flat and specularly reflecting;

b) generally orienting said ellipsometer source of a beam of electromagnetic radiation so that it directs a beam of electromagnetic radiation onto a first location of said alignment sample at an oblique angle, which beam then reflects from said alignment sample and enters said data detector so that it provides an output signal.

The is followed by itteratively repeating steps itteratively repeating steps c1, c2 and c3 in any functional order until the output of the data detector is substantially the same in all said steps c1, c2 and c3, said steps c1, c2 and c3 being:

c1) while monitoring the output signal from said data detector causing said stage to effect translation of said alignment sample so that said beam is directed to a second location thereon at said oblique angle, reflects therefrom and enters said data detector, followed by adjusting the tip/tilt of said stage;

c2) while monitoring the output signal from said data detector causing said stage to effect translation of said alignment sample so that said beam is directed to a third location thereon at said oblique angle, reflects therefrom and enters said data detector, followed by adjusting the tip/tilt of said stage, said third location being other than co-linear with said first and second locations;

c3) while monitoring the output signal from said data detector causing said stage to effect translation of said alignment sample so that said beam is directed to a said first location thereon at said oblique angle, reflects therefrom and enters said data detector, followed by adjusting the tip/tilt of said stage;

with the result being that the stage is oriented in tip/tilt so that no matter from what location on said alignment sample said beam is caused to reflect, the output from said data detector remains substantially the same;

said method can then further comprises the step of:

d) while monitoring the data detector output signal moving the location and orientation thereof until said output signal therefrom is substantially maximized, to optimally position said data detector.

Said method can further comprise itteratively repeating a step c4 along with steps c1, c2 and c3, said step c4 being:

c4) while monitoring the output signal from said data detector causing said stage to effect translation of said alignment sample so that said beam is directed to a forth location thereon at said oblique angle, reflects therefrom and enters said data detector, followed by adjusting the tip/tilt of said stage.

It is noted that where four locations are used the preferred approach is to position then as corners of a square oriented about a central region of the sample.

It is also noted that to improve results said ellipsometer system preferably further comprises a focusing lens between said ellipsometer source of a beam of electromagnetic radiation and said stage.

Said method further can further comprise:

e) providing and positioning a source of a beam of electromagnetic radiation derived from a selection from the group consisting of:
  said ellipsometer source of a beam of electromagnetic radiation; and
  an alternative source of a beam of electromagnetic radiation;

such that it provides an alignment beam of electromagnetic radiation which proceeds substantially along an incident locus which is normal to said alignment sample, which then reflects from said alignment sample and returns substantially back along the incident locus; and providing a normal beam monitoring multi-detector element alignment detector so that it monitors said reflected alignment beam of electromagnetic radiation, and positioning it such that each detector element of said normal beam monitoring multi-detector element alignment detector provides no output signal or such that each detector element of said normal beam monitoring multi-detector element alignment detector provides reference output signals when said normally reflected alignment beam of electromagnetic radiation interacts therewith, said normal beam monitoring multi-element alignment detector being selected from the group consisting of:
  it comprises a plurality of detector elements surrounding a central hole through which said alignment beam passes, said detector elements being positioned to monitor said alignment beam after it reflects from said sample; and
  it comprises a plurality of detector elements in combination with a beam spliter, said beam spliter being positioned to intercept said beam which reflects from said sample and direct a portion thereof toward said alignment beam monitoring detector elements;

f) removing said alignment sample from said stage and placing a second sample thereupon;

g) adjusting the locations of said ellipsometer source of a beam of electromagnetic radiation and data detector and alignment detector, and/or the tip/tilt of said stage so that the normal beam monitoring multi-detector element alignment detector provides no output signals or such that each detector element of said normal beam monitoring multi-detector element alignment detector provides said reference output signals; and h) optionally simultaneous with adjusting the tip/tilt of said stage effecting translation thereof to maintain unchanged the location on said second sample at which said oblique beam reflects therefrom.

(Note, the reference signals in step e can all be zero, or any combination of zero and non-zero values, or can all be non-zero values which the alignment detector produces when the alignment sample is properly aligned. And, in step f, it is to be understood that while the preferred and simpler approach is to align the stage/sample by tip/tilt of the stage, it is possible to alternatively or in combination with effecting tip/tilt of the stage, move the locations of said ellipsometer source of a beam of electromagnetic radiation and data detector and alignment detector to accomplish said alignment).

Once steps a-d of the method have been accomplished, the presence of said normal beam monitoring multi-detector element alignment detector as described allows easy alignment of second and follow-on samples without the necessity to repeat steps a-d. That is, only steps f-g or h then need be practiced to accurately align said second and follow-on samples.

It is noted that output signal from a data detector was recited in the foregoing. It is possible to replace said data detector with an oblique beam monitoring multi-element alignment detector of electromagnetic radiation such as a selection from the group consisting of:
  it comprises a plurality of detector elements surrounding a central hole toward which said beam is directed after it reflects from said sample; and
  it comprises a plurality of detector elements in combination with a beam spliter, said beam spliter being positioned to intercept said beam which reflects from said sample and direct a portion thereof toward said oblique beam monitoring multi-element alignment detector.

The method recited above remains the same, but signals from the plurality of elements of the oblique beam monitoring multi-element alignment detector of electromagnetic radiation are monitored, and the goal is to orient said stage so that the detector elements provide no output signals, or such that each detector element of said normal beam monitoring multi-detector element alignment detector provides reference output signals.

Typical practice is to cause the oblique angle beam of electromagnetic radiation provided by said ellipsometer source of a beam of electromagnetic radiation and said normal angle alignment beam derived from said ellipsometer source of a beam of electromagnetic radiation or an alternative source of a beam of electromagnetic radiation are caused to impinge on said alignment and/or second sample at the same location.

It is also mentioned that said method can involve providing actuators which receive signals from the oblique angle beam and alignment detector and produce stage position and orientation controlling motions, and in which said steps g and h are automated.

Additional present invention methodology of aligning a beam of electromagnetic radiation onto a sample surface comprises:

a) causing a beam of electromagnetic radiation to impinge upon a sample surface at an oblique angle of incidence such that it reflects into a data detector, said reflected beam optionally passing through a central hole in a multiple element alignment detector or being reflected onto a multiple element alignment detector;

b) causing said sample to be tilted/tipped to realize a selection from the group consisting of:
   the data detector signal is maximized; and
   the signals from the multiple elements of a multiple element alignment detector through which said beam is caused to pass or is reflected onto are essentially equal;

c) at the same oblique angle of incidence, placing focusing and recollimating lenses into the pathway of said electromagnetic beam before and after said sample, respectively, and causing said sample to be raised or lowered such that a selection from the group consisting of:
   the data detector signal is maximized; and
   the signals from the multiple elements of a multiple element detector through which said beam is caused to pass or is reflected onto are essentially equal.

Said steps b and c are itteratively repeated a plurality of times at a selection from the group consisting of:
   the same location on the sample surface; and
   a plurality of locations on the sample surface;

to improve alignment.

Said method can further include providing feedback/actuator means; said feedback means being applied to receive at least one signal from at least one selection from the group consisting of:
   said data detector; and
   said alignment detector;

and wherein said actuator means effects sample tilt/tip and/or sample raising or lowering in steps b and c by automatic response to said received at least one signal.

Importantly, said method can further comprises the step of:

d) removing the focusing lenses from the pathway of said beam of electromagnetic radiation and acquiring sample describing data from said data detector.

The presence of the lenses is important during stage alignment, but less so during data acquisition.

It is noted that electromagnetic radiation can be entered to the data detector via a fiber optic, thereby providing a relatively small target for the focused electromagnetic beam in step c.

It is also to be appreciated that the alignment beam of electromagnetic radiation provided by a selection from the group consisting of:
   said source of a beam of spectroscopic electromagnetic radiation; and
   an alternative source a beam of electromagnetic radiation;

and an alignment detector can be present, with said alignment detector being positioned to detect when said sample is oriented so that said alignment beam approaches said sample surface so that, at the point of reflection therefrom, it reflects directly back along its incident trajectory, the purpose being to enable orienting said sample surface in a known orientation.

Said method can include applying a beam modulator to modulate at least one selection from the group consisting of:
   said spectroscopic electromagnetic beam; and
   said alignment beam;

to distinguish said at least one selection from external light, thereby enabling use in rooms illuminated by non-modulated light in which the electromagnetic beam is modulated to distinguish it from external light, to enable use in lit rooms.

Another present invention method of aligning a beam of electromagnetic radiation onto a sample comprises:

a) providing a system comprising:
   source of a beam of spectroscopic electromagnetic radiation;
   stage for supporting a sample;
   data detector of spectroscopic electromagnetic radiation;
   said system further comprising, between said source and stage, means for receiving a beam of spectroscopic electromagnetic radiation from said source thereof and providing it to the surface of a sample on said stage at any of at least two angles-of-incidence to said surface, with at least one of said angles-of-incidence being available as a focused and as a non-focused beam onto said sample surface;
   said system being characterized by at least one selection from the group consisting of:
   said system being characterized by at least one selection from the group consisting of:
      said stage for supporting said sample comprises means for moving said sample in two orthogonal directions in a plane parallel to said sample surface; and
      the presence of means for moving as a group, said source, data detector and means for receiving a beam of spectroscopic electromagnetic radiation from said source thereof and providing it to a sample on said stage, in two orthogonal directions in a plane substantially parallel to said sample surface;
      the presence of means for moving the sample in a direction to place it closer to or further away from said source, data detector, and said means for receiving a beam of spectroscopic electromagnetic radiation from said source thereof, and providing it to a sample on said stage;
   said system further comprising means for controlling stage tip/tilt and therefor the orientation of the plane in which said sample surface is present, and
   said system optionally further comprising means for causing rotation of said sample;
   said system further comprising means for providing an alignment beam of electromagnetic radiation provided by a selection from the group consisting of:
      said source of a beam of spectroscopic electromagnetic radiation; and
      an alternative source a beam of electromagnetic radiation;

and an alignment detector, said alignment beam and detector being oriented and positioned to detect when said sample is oriented and with a normal to its surface projecting such that said alignment beam approaches said sample surface and, at the point of reflection therefrom, reflects directly back upward along its incident trajectory, there being a known relationship between the loci of said alignment and said beam of spectroscopic electromagnetic radiation.

Said method proceeds with:

b) placing a sample on said stage and causing an alignment beam of electromagnetic radiation to impinge upon a sample at a substantially normal angle to a surface of said sample, such that it reflects from said sample surface into said alignment detector, and causing said stage to cause said sample surface to be tilted/tipped such that the signals from the alignment detector indicate that said alignment beam of electromagnetic radiation caused to impinge upon the surface of said sample reflects therefrom along a normal angle to said sample surface;

c) causing a beam of spectroscopic electromagnetic radiation to approach the surface of said sample at an oblique angle thereto, and placing focusing lenses before and after said sample into the pathway of said spectroscopic beam of electromagnetic, and optionally placing and orienting a second alignment detector to monitor reflected spectroscopic electromagnetic radiation from said sample surface, then causing said sample to be moved along a locus substantially perpendicular to a normal to said sample surface, such that a selection from the group consisting of:

the data detector signal strength is maximized; and signals from said second alignment detector indicate that the reflected beam is directed to substantially maximize data detector signal strength.

Steps b and c can be itteratively repeated a plurality of times at a selection from the group consisting of:

the same location on the sample surface; and a plurality of locations on the sample surface;

to improve alignment of said spectroscopic electromagnetic beam.

Effecting tilt/tip and sample raising or lowering in steps b and c can be effected by automatic systems which utilize feedback from said data detector and/or optionally, said alignment detectors.

Said method can further comprise the step of:

d) removing the focusing lenses from the pathway of said beam of electromagnetic radiation and acquiring sample describing data from said data detector.

And said method can involve entering electromagnetic radiation is to the data detector via a fiber optic, thereby providing a relatively small target for the focused electromagnetic beam in step c.

Another method of aligning an ellipsometer system which comprises:

an ellipsometer source of a beam of electromagnetic radiation;

a stage for supporting a sample and having means for effecting tip/tilt and translation thereof;

a data detector of electromagnetic radiation;

comprises the steps:

a) placing an alignment sample on said stage;

b) generally orienting said ellipsometer source of a beam of electromagnetic radiation so that it directs a beam of electromagnetic radiation onto a first location of said alignment sample at an oblique angle, which beam then reflects from said alignment sample and enters said data detector so that it provides an output signal;

itteratively repeating steps c1, c2 and c3 in any functional order until the output of the data detector is substantially the same in all said steps c1, c2 and c3, said steps c1, c2 and c3 being:

c1) while monitoring the output signal from said data detector causing said stage to effect translation of said alignment sample so that said beam is directed to a second location thereon at said oblique angle, reflects therefrom and enters said data detector, followed by adjusting the tip/tilt of said stage;

c2) while monitoring the output signal from said data detector causing said stage to effect translation of said alignment sample so that said beam is directed to a third location thereon at said oblique angle, reflects therefrom and enters said data detector, followed by adjusting the tip/tilt of said stage, said third location being other than co-linear with said first and second locations;

c3) while monitoring the output signal from said data detector causing said stage to effect translation of said alignment sample so that said beam is directed to a said first location thereon at said oblique angle, reflects therefrom and enters said data detector, followed by adjusting the tip/tilt of said stage;

with the result being that the stage is oriented in tip/tilt so that no matter from what location on said alignment sample said beam is caused to reflect, the output from said data detector remains substantially the same.

Said method then optionally further comprises:

d) while monitoring the data detector output signal moving the location and orientation thereof until said output signal therefrom is substantially maximized.

Said method can which further comprise itteratively repeating a step c4 along with steps c1, c2 and c3, said step c4 being selected from the group consisting of c4a and c4b:

c4a) while monitoring the output signals from the detector elements of said oblique beam monitoring multi-element alignment detector, causing said stage to effect translation of said sample so that said beam is directed to a forth, arbitrary, location thereon at said oblique angle, reflects therefrom and enters said multi-element alignment detector, followed by adjusting the tip/tilt of said stage.

c4b) while monitoring the output signals from the detector elements of said oblique beam monitoring multi-element alignment detector, causing said stage to effect translation of said sample so that said beam is directed to a forth, location thereon at said oblique angle, reflects therefrom and enters said multi-element alignment detector, followed by adjusting the tip/tilt of said stage, said forth location being oriented so as to form a square shape with the first three locations.

Said ellipsometer system applied in said method can further comprise a focusing lens between said ellipsometer source of a beam of electromagnetic radiation and said stage.

Said method can further comprise:

e) providing and positioning a source of a beam of electromagnetic radiation derived from a selection from the group consisting of:

said ellipsometer source of a beam of electromagnetic radiation; and an alternative source of a beam of electromagnetic radiation;

such that it provides an alignment beam of electromagnetic radiation which proceeds substantially along an incident locus which is normal to said alignment sample, which then reflects from said alignment sample and returns substantially back along the incident locus; and providing a normal beam monitoring multi-detector element alignment detector so that it monitors said reflected alignment beam of electromagnetic radiation, and positioning it such that each detector element of said normal beam monitoring multi-detector element alignment detector provides no output signal or such that each detector element of said normal beam monitoring multi-detector element alignment detector provides reference output signals when said reflected alignment beam of electromagnetic radiation normally interacts therewith, said normal beam monitoring multi-element alignment detector being selected from the group consisting of:

it comprises a plurality of detector elements surrounding a central hole through which said alignment beam passes, said detector elements being positioned to monitor said alignment beam after it reflects from said sample; and it comprises a plurality of detector elements in combination with a beam spliter, said beam spliter being positioned to intercept said beam which reflects from said sample and direct a portion thereof toward said alignment beam monitoring detector elements;

f) removing said alignment sample from said stage and placing a second sample thereupon;

g) adjusting the locations of said ellipsometer source of a beam of electromagnetic radiation and data detector and alignment detector, and/or the tip/tilt of said stage so that the normal beam monitoring multi-detector element alignment detector provides no output signals or such that each detector element of said normal beam monitoring multi-detector element alignment detector provides said reference output signals; and h) optionally simultaneous with adjusting the tip/tilt of said stage effecting translation thereof to maintain unchanged the location on said second sample at which said oblique beam reflects therefrom.

Another method of aligning an ellipsometer system which comprises:

an ellipsometer source of a beam of electromagnetic radiation;

a stage for supporting a sample and having means for effecting tip/tilt and translation thereof;

an oblique beam monitoring multi-element data detector of electromagnetic radiation;

comprises the steps:

a) placing a sample on said stage;

b) generally orienting said ellipsometer source of a beam of electromagnetic radiation so that it directs a beam of electromagnetic radiation onto a first location of said alignment sample at an oblique angle, which beam then reflects from said alignment sample and enters said data detector so that it provides an output signal;

itteratively repeating steps c1, c2 and c3 in any functional order until the output of the data detector is substantially the same in all said steps c1, c2 and c3, said steps c1, c2 and c3 being:

c1) while monitoring the output signal from said data detector causing said stage to effect translation of said alignment sample so that said beam is directed to a second location thereon at said oblique angle, reflects therefrom and enters said data detector, followed by adjusting the tip/tilt of said stage;

c2) while monitoring the output signal from said data detector causing said stage to effect translation of said alignment sample so that said beam is directed to a third location thereon at said oblique angle, reflects therefrom and enters said data detector, followed by adjusting the tip/tilt of said stage, said third location being other than co-linear with said first and second locations;

c3) while monitoring the output signal from said data detector causing said stage to effect translation of said alignment sample so that said beam is directed to a said first location thereon at said oblique angle, reflects therefrom and enters said data detector, followed by adjusting the tip/tilt of said stage;

with the result being that the stage is oriented in tip/tilt so that no matter from what location on said alignment sample said beam is caused to reflect, the output from said data detector remains substantially the same;

d) optionally while monitoring the outputs from said detector elements of said oblique beam monitoring multi-element alignment detector, moving the location and orientation thereof until said output signals therefrom are substantially optimized.

Again, said method can further comprise itteratively repeating a step c4 along with steps c1, c2 and c3, said step c4 being selected from the group consisting of c4a and c4b:

c4a) while monitoring the output signals from the detector elements of said oblique beam monitoring multi-element alignment detector, causing said stage to effect translation of said sample so that said beam is directed to a forth, arbitrary, location thereon at said oblique angle, reflects therefrom and enters said multi-element alignment detector, followed by adjusting the tip/tilt of said stage.

c4b) while monitoring the output signals from the detector elements of said oblique beam monitoring multi-element alignment detector, causing said stage to effect translation of said sample so that said beam is directed to a forth, location thereon at said oblique angle, reflects therefrom and enters said multi-element alignment detector, followed by adjusting the tip/tilt of said stage, said forth location being oriented so as to form a square shape with the first three locations.

And again said method can provide that said ellipsometer system further comprise a focusing lens between said ellipsometer source of a beam of spectroscopic electromagnetic radiation and said stage.

Said oblique beam monitoring multi-element alignment detector can be selected from the group consisting of:

it comprises a plurality of detector elements surrounding a central hole toward which said beam is directed after it reflects from said sample; and it comprises a plurality of detector elements in combination with a beam spliter, said beam spliter being positioned to intercept said beam which reflects from said sample and direct a portion thereof toward said oblique beam monitoring multi-element alignment detector.

Said method can further comprise:

e) providing and positioning a source of a beam of electromagnetic radiation derived from a selection from the group consisting of:
    said ellipsometer source of a beam of electromagnetic radiation; and
    an alternative source of a beam of electromagnetic radiation;
  such that it provides an alignment beam of electromagnetic radiation which proceeds substantially along an incident locus which is normal to said alignment sample, which then reflects from said alignment sample and returns substantially back along the incident locus; and providing a normal beam monitoring multi-detector element alignment detector so that it monitors said reflected alignment beam of electromagnetic radiation, and positioning it such that each detector element of said normal beam monitoring multi-detector element alignment detector provides no output signal or such that each detector element of said normal beam monitoring multi-detector element alignment detector provides reference output signals when said reflected alignment beam of electromagnetic radiation normally interacts therewith, said normal beam monitoring multi-element alignment detector being selected from the group consisting of:

it comprises a plurality of detector elements surrounding a central hole through which said alignment beam passes, said detector elements being positioned to monitor said alignment beam after it reflects from said sample; and it comprises a plurality of detector elements in combination with a beam spliter, said beam spliter being positioned to intercept said beam which reflects from said sample and direct a portion thereof toward said alignment beam monitoring detector elements;

f) removing said alignment sample from said stage and placing a second sample thereupon;

g) adjusting the locations of said ellipsometer source of a beam of electromagnetic radiation and data detector and alignment detector, and/or the tip/tilt of said stage so that the normal beam monitoring multi-detector element alignment detector provides no output signals or such that each detector element of said normal beam monitoring multi-detector element alignment detector provides said reference output signals; and h) optionally simultaneous with adjusting the tip/tilt of said stage effecting translation thereof to maintain unchanged the location on said second sample at which said oblique beam reflects therefrom.

In the above methods said oblique angle beam of electromagnetic radiation provided by said ellipsometer source of a beam of electromagnetic radiation and said normal angle alignment beam derived from said ellipsometer source of a beam of electromagnetic radiation or an alternative source of a beam of electromagnetic radiation can be caused to impinge on said alignment and/or second sample at the same location.

The methodology presented above can provide that actuators are provided which receive signals from the data and alignment detector elements and produce stage position and orientation controlling motions, and in which said steps g and h are automated.

Continuing, it is to be understood that while ellipsometers are used as a primary example, the present invention can be practiced with a system selected from the group consisting of:
reflectometer;
rotating analyzer ellipsometer;
rotating polarizer ellipsometer;
rotating compensator ellipsometer;
modulation element ellipsometer;
Mueller Matrix measuring system;

which operates at least one wavelength in at least one wavelength range, such as:
VUV;
UV;
Visible;
Infrared;
Far Infrared;
Radio Wave.

Said system can be a spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one Pseudo-Achromatic compensator(s) positioned at a location selected from the group consisting of:
before said stage for supporting a material system;
after said stage for supporting a material system; and
both before and after said stage for supporting a material system.

Said selected system can further comprise means for flowing purging gas onto said sample at a location thereon at which electromagnetic radiation of UV and/or IR wavelengths is caused to impinge.

Said system can further comprises at least one electromagnetic beam intercepting angle-of-incidence changing system comprising elements which are easily functionally entered into the locus of the electromagnetic beam on both sides of said sample system, which at least one electromagnetic beam intercepting angle-of-incidence changing system serves to direct said electromagnetic beam onto substantially the same spot on the sample system as is the case where the said at least one electromagnetic beam intercepting angle-of-incidence changing system is not functionally present, but at an angle-of-incidence which is different than that when said at least one electromagnetic beam intercepting angle-of-incidence changing system is not functionally present, said at least one electromagnetic beam intercepting angle-of-incidence changing system not effecting, or requiring change of, the locus of the electromagnetic beams outside said at least one electromagnetic beam intercepting angle-of-incidence changing system, on either side of said means for supporting a sample system, hence does not require said material system investigating system to comprise multiple sources and detectors or the change of position of at least one selection from the group consisting of:
said source of electromagnetic radiation; and
said detector thereof;

to effect change said angle-of-incidence;

said material system investigating system being functionally mounted to a two dimension location means for positioning said selected system at points in an two dimensional plane which is, in use, oriented substantially parallel to but offset from, the plane of a surface of said sample system;

such that in use said selected system is located near the surface of said sample and a beam of electromagnetic radiation provided by said source means is caused to interact therewith and enter said data detector means;

said selected system further comprising means for adjusting the location thereof at desired third dimension offset locations with respect to points in said plane of the surface of said sample; and said selected system further comprising means for controlling the location of the source means and data detector means in said two dimension plane.

Said at least one electromagnetic beam intercepting angle-of-incidence changing system can comprise, on each side of said means for supporting a sample system, at least one selection from the groups consisting of:
 multiple angle prism(s); and
 a system of mirrors;

said at least one electromagnetic beam intercepting angle-of-incidence changing system being slideably mounted to a guide element such that the functional presence thereof in the pathway of the locus of the electromagnetic beams on both sides of said means for supporting a sample system is effected by physical sliding motion of said at least one electromagnetic beam intercepting angle-of-incidence changing system along said guide element.

Said at least one electromagnetic beam intercepting angle-of-incidence changing system can comprise a first multiangle prism on the incident side of said means for supporting a sample system and a second multiangle prism thereafter, said first and second multiangle prisms each having a first and a second side, each said multiangle prism presenting with first and second inner surfaces associated with said first and second sides, respectively, the first and second side of each multiangle prism having means for changing the properties of inner surface thereof from essentially transmissive to essentially reflective, each said multiangle prism being oriented such that an electromagnetic beam entering thereinto encounters the first or second inner surface thereof and either passes therethrough and progresses on to contact a sample system placed on said means for supporting a sample system, or reflects from said first or second inner surface thereof and then from said second or first inner surface thereof, respectively, and then progresses on to contact a sample system placed on said means for supporting a sample system. And said system can further comprise at least one shutter door which can be opened to let the electromagnetic beam pass, or closed to block its passage, said at least one shutter door being positioned in the electromagnetic beam locus selected from the group consisting of:
 defined by passage through said first or second side of said first multiangle prism; and
 defined by reflection from said first or second side of said first multiangle prism;

said at least one shutter door being positioned between at least one selection from the group consisting of:
 said first multiangle prism and the means for supporting a sample system; and
 said means for supporting a sample system and said second multiangle prism.

Said at least one electromagnetic beam intercepting angle-of-incidence changing system can comprise, on first and second sides of said means for supporting a sample system, first and second beam splitters, respectively, which first and second beam splitters each pass approximately half, and reflect approximately half of a beam of electromagnetic radiation caused to be incident thereupon at an oblique angle to a surface thereof; said at least one electromagnetic beam intercepting angle-of-incidence changing system further comprising a first reflective means positioned to intercept the approximately half of the electromagnetic beam which reflects from said first beam splitter on the incident side of said means for supporting a sample system and direct it toward said means for supporting a sample system; and also further comprising a second reflective means positioned after said means for supporting a sample system to intercept an electromagnetic beam which reflects from a sample system placed on said means for supporting a sample system and direct it toward the second beam splitter;

said material system investigating system further comprising at least one shutter door which can be opened to let the electromagnetic beam pass, or closed to block its passage, said at least one shutter door being positioned in the pathway of the electromagnetic beam between which progresses along a locus selected from the group consisting of:
 defined by passage through said first beam splitter; and
 defined by reflection from said first beam splitter;

on either side of said means for supporting a sample system.

Said system can include at least two multiple angle prisms, one being present on one side of said sample system, and the other thereof being present on the other side of said sample system.

Said system can include focusing optic positioned to focus a beam of electromagnetic radiation onto a sample system.

Said system can include means for adjusting the orientation of at least one electromagnetic beam intercepting angle-of-incidence changing system, optionally in simultaneous combination which includes focusing optics positioned to focus a beam of electromagnetic radiation onto a sample system and recollimate the beam of electromagnetic radiation which reflects from said sample system.

Said at least one electromagnetic beam intercepting angle-of-incidence changing system can comprise, on at least one side selected from the group consisting of:
 said first and;
 said second;

sides of said means for supporting a sample system, at least one system of mirrors, said at least one system of mirrors being comprised of:

a means for changing the propagation direction of an initial beam of electromagnetic radiation without significantly changing the phase angle between orthogonal components thereof, said means comprising two pairs of reflecting mirrors oriented so that said initial beam of electromagnetic radiation reflects from a first reflecting means in the first pair of reflecting means to a second reflecting means in said first pair of reflecting means, in a first plane; and such that the beam of electromagnetic radiation which reflects from the second reflecting means in said first pair of reflecting means reflects from the first reflecting means in said second pair of reflecting means to said second reflecting means in said second pair of reflecting means, in a second plane which is essentially orthogonal to said first plane; such that the direction of propagation of the beam of electromagnetic radiation reflected from the second reflecting means in said second pair of reflecting means is different from the propagation direction of the initial beam of electromagnetic radiation; the basis of operation being that changes entered between the orthogonal components by the first pair of reflective means is canceled by that entered by the second pair of reflective means.

For further insight, it is to be understood that the present invention can comprise a system for application in investigating a sample system with electromagnetic radiation, sequentially comprising:
 a. a source of a beam electromagnetic radiation;
 b. a polarizer element;
 c. optionally a compensator element;
 d. additional element(s);
 e. a sample system;
 f. additional element(s);
 g. optionally a compensator element;

h. an Analyzer element; and i. a Detector System;

wherein said additional component(s) in d. and f. each comprise at least one electromagnetic beam intercepting angle-of-incidence changing system element which can be easily entered into the locus of the electromagnetic beam on both sides of said sample system, which at least one electromagnetic beam intercepting angle-of-incidence changing system elements serves to direct said electromagnetic beam onto substantially the same spot on the sample system as is the case where the said at least one electromagnetic beam intercepting angle-of-incidence changing system elements are not present, but at an angle-of-incidence which is different than that when said at least one electromagnetic beam intercepting angle-of-incidence changing system is not present, said at least one electromagnetic beam intercepting angle-of-incidence changing system elements not effecting, or requiring change of, the locus of the electromagnetic beams outside said at least one electromagnetic beam intercepting angle-of-incidence changing system elements, on either side thereof, hence does not require multiple sources and detectors or change of position of at least one selection from the group consisting of:

said source of electromagnetic radiation; and said detector thereof;

to effect change said angle-of-incidence;

said material system investigating system being functionally mounted to a two dimension location means for positioning said selected system at points in an two dimensional plane which is, in use, oriented substantially parallel to but offset from, the plane of a surface of said sample system;

such that in use said selected system is located near the surface of said sample and a beam of electromagnetic radiation provided by said source means is caused to interact therewith and enter said data detector means;

said selected system further comprising means for adjusting the location thereof at desired third dimension offset locations with respect to points in said plane of the surface of said sample; and said selected system further comprising means for controlling the location of the source means and data detector means in said two dimension plane.

Said system can provide that each electromagnetic beam intercepting angle-of-incidence changing system is a selection from the group consisting of:

multiangle prisms; and a plurality of mirrors.

Said system can comprises a means for setting the angle of incidence of a beam of electromagnetic radiation comprising, as viewed in elevation, first and second arms pivotally interconnected to one another at an upper aspect thereof by a first pivot means, said first and second arms projecting downward and to the left and right of said first pivot means; distal ends of said first and second arms being pivotally affixed to third and forth arms, said third and forth arms being pivotally interconnected to one another by a second pivot means at a lower aspect thereof, said third and forth arms being projected upward and to the left and right of said second pivot means at said lower aspect thereof; there being at least two substantially downward projecting arms pivotally affixed to each of said third and forth arms, distal ends of which are pivotally affixed to fifth and sixth arms which are not interconnected to one another, but project upward to the left and right, respectively;

there being affixed to one of said fifth and sixth arms a source of a beam of electromagnetic radiation, and to the other of said sixth and fifth arms a detector of said beam of electromagnetic radiation;

there further being a sample located such that a beam of electromagnetic radiation produced by said source of a beam of electromagnetic radiation reflects from an upper surface of said sample and enters said detector of said beam of electromagnetic radiation;

such that in use when the first pivot means at which said first and second arms are interconnected is caused to be vertically raised or lowered, the angle of incidence at which the beam of electric radiation approaches said sample surface is changed, but the location at which it interacts with said sample surface remains substantially unchanged.

Said system can comprise one electromagnetic beam intercepting angle-of-incidence changing system comprising elements which are easily functionally entered into the locus of the electromagnetic beam on one side of said sample system, which one electromagnetic beam intercepting angle-of-incidence changing system serves to direct said electromagnetic beam to, or receive said electromagnetic beam from substantially the same spot on the sample system as is the case where the said one electromagnetic beam intercepting angle-of-incidence changing system is not functionally present.

The present invention will be better understood by reference to the Detailed description Section of this Disclosure, in combination with the Drawings.

SUMMARY OF THE INVENTION

It is a purpose and/or objective of the present invention to disclose ellipsometer or the like systems comprising means to, for instance, allow easy changing of a beam angle-of-incidence and plane-of-incidence, and methodology for aligning samples in said ellipsometer and the like systems.

Otherwise stated, it is a purpose and/or objective of the present invention to disclose system and method for aligning a sample tip/tilt orientation and height, so that a beam of electromagnetic radiation caused to approach a surface thereof at a known angle and plane of incidence, reflects therefrom and enters a data detector.

Other purposes and/or objectives of the present invention will be apparent from a reading of the disclosure in conjunction with the drawings, and claims.

BRIEF DESCRIPTION OF THE DRAWINGS

FIG. 6ed demonstrates an irregular sample surface.

FIG. 17b shows a modified version of the system of FIG. 17a.

DETAILED DISCLOSURE

The present disclosure is of new systems and methodology for alignment of both tilt, and vertical positioning of samples in ellipsometer and the like systems, which are well suited for automated operation.

While sample tip/tilt and height adjustments can be conducted using an electromagnetic beam which is caused to impinge on a sample at an oblique angle of incidence, (see FIG. 7a), perhaps in an itterative manner, a more convenient approach involves adjusting tip/tilt using a beam directed to be incident on a sample along a normal to the surface thereof, and reflect into a multiple element (eg. Quad-detector). Adjustment of tip/tilt in such an arrangement can be conducted to the point that equal signals are provided from each element of the multiple elements, which indicates that the sample surface is facing directly upward. Adjustment of the height of the sample can not be achieved by use of a normally directed beam, however, as the beam directed at normal incidence is insensitive to height. A beam directed to approach the sample at an oblique angle of incidence, (eg. an ellipsometer beam), is best suited to use in adjusting the height of the sample. The method of adjustment can involve monitoring the output of a data detector and adjusting sample height until it peaks, or can involve use multiple element detectors and monitoring the output from each of the elements until they are equal, (again see FIG. 7a elements (DET) and (AD) respectively). Further, while two sources, (eg. see FIG. 6c (LS) and (LS')), of electromagnetic beams of electromagnetic radiation can be applied to effect, respectively, tip/tilt and height locationing of samples, an approach which utilizes a single source thereof, (eg. see FIGS. 1-5), combined with beam splitters/director and the like, offer utility.

Figure 1:
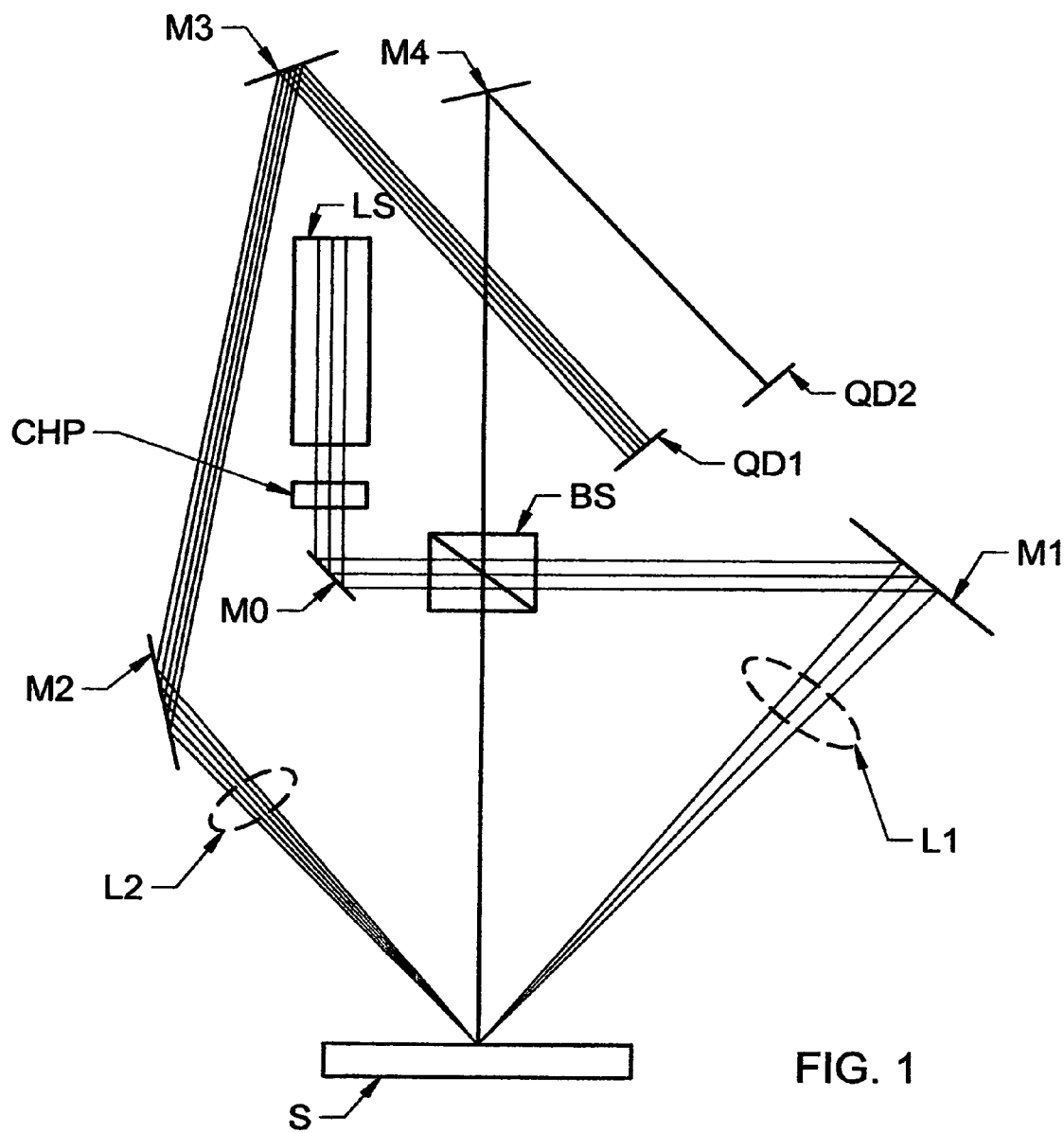
FIG. 1 shows a first embodiment of a disclosed invention sample alignment system.

Turning now to FIG. 1, a first sample alignment system embodiment comprises:
    a) a source (LS) of electromagnetic radiation;
    b) a beam splitter (BS);
    c) at least first (M1) mirror and optionally additional (eg. second (M2), third (M3) and forth (M4) mirrors);
    d) first (QD1) and second (QD2) alignment detectors;
    e) at least focusing (L1) and collimating (L2) lenses; and
    e) a stage for supporting a sample (S).

Said source (LS) of electromagnetic radiation is positioned to direct a beam of electromagnetic radiation toward said beam splitter (BS). Said beam splitter (BS) is positioned to direct a first portion of said beam toward said first mirror (M1), which reflects said first portion of said beam through said focusing lens (L1) and obliquely onto said sample (S) such that it impinges at substantially to same location at which the second portion of said beam, which is directed normally toward said sample (S), impinges. Said second portion of said beam is reflected from said sample (S) substantially directly back along the path of its incidence, through said beam splitter (BS) and into said second alignment detector (QD2). Said first portion of said beam is reflected from said sample (S), through said collimating lens (L2) and into said first alignment detector (QD1).

Said first embodiment can further comprise at least one selection from the group consisting of:
    a beam directing mirror (M0) between said light source (LS) and said beam splitter (BS);

at least one beam directing mirror ((M2) and/or (M3)) between said collimating lens (L2) and said first alignment detector (QD1);
at least one beam directing mirror (M4) between said beam splitter (BS) and said second alignment detector (QD2).

Figure 2:
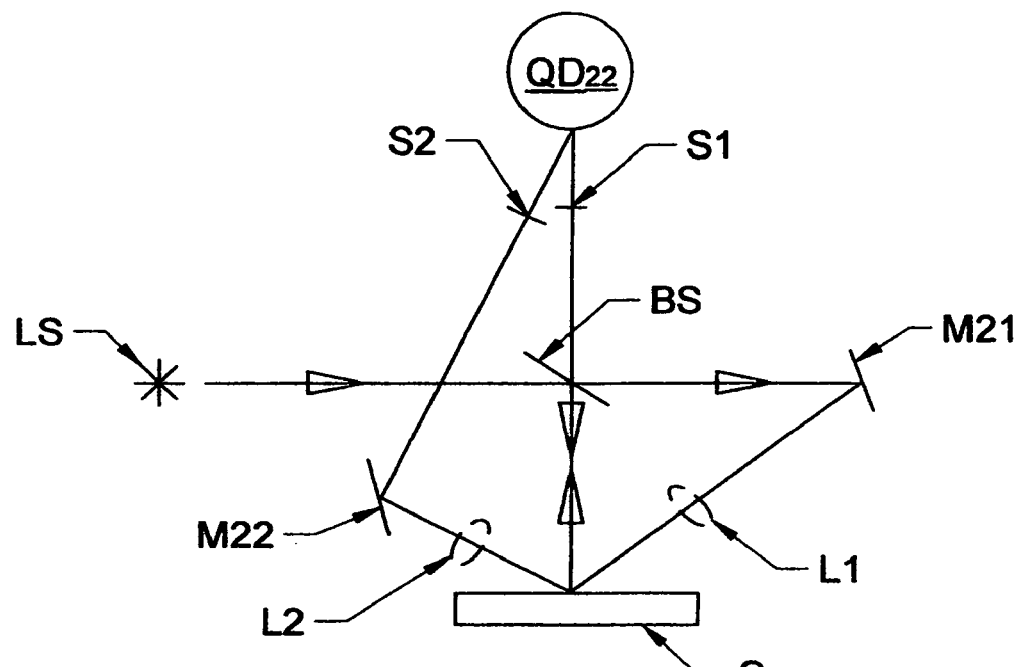
FIG. 2 shows a second embodiment of a disclosed invention sample alignment system.

Turning now to FIG. 2, a second sample alignment system embodiment comprises:
a) a source of electromagnetic radiation (LS);
b) a beam splitter (BS);
c) at least first (M21) and second (M22) mirrors;
d) an alignment detector (QD22);
e) first and second shutters (S1) and (S2); and
f) a stage for supporting a sample (S).

Said beam splitter (BS) is positioned to direct a first portion of a beam of electromagnetic radiation from said source (LS) thereof normal onto said sample (S) and a second portion thereof toward said first mirror (M21) which reflects it onto said sample (S) at an oblique angle such that it impinges thereupon at substantially the same location at which the first portion of said beam impinges. Said first portion of said beam, after normally reflecting from said sample (S) is directed back along the path of its incidence, through said beam splitter (BS) and toward said alignment detector (QD22). Said second portion of said beam, after obliquely reflecting from said sample (S), is directed to reflect from said second mirror (M22) toward said alignment detector (QD22). Said first shutter (S1) is in the pathway of said beam which passes through said beam splitter (BS) toward said alignment detector (QD22), and said second shutter (S2) is in the pathway of said beam which reflects from said second mirror (M22). In use said shutters (S1) (S2) are operated to sequentially allow entry into said alignment detector (QD22) of electromagnetic radiation:
normally reflected from said sample (S) and directed back along the path of its incidence, through said beam splitter (BS) and toward said alignment detector (QD22); and
obliquely reflected from said second mirror (M22) toward said alignment detector (QD22).

Figure 3:
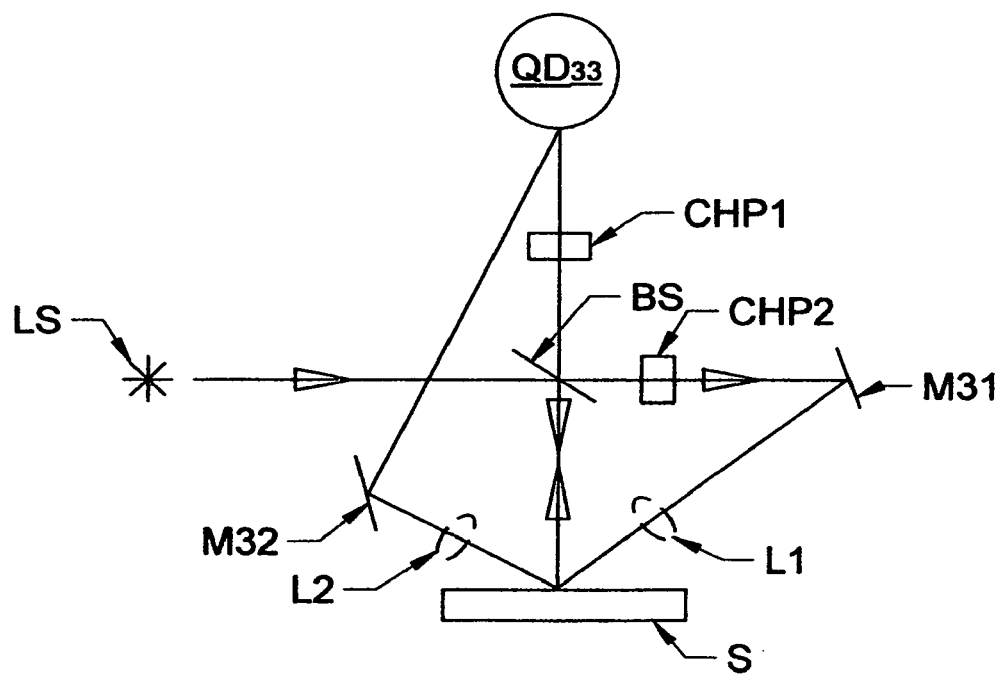
FIG. 3 shows a third embodiment of a disclosed invention sample alignment system.

Turning now to FIG. 3, a third sample alignment system embodiment comprises:
a) a source of electromagnetic radiation (LS);
b) a beam splitter (BS);
c) at least first (M21) and second (M22) mirrors;
d) an alignment detector (QD33);
e) first and second choppers (CHP1)) and (CHP2); and
f) a stage for supporting a sample (S).

Said beam splitter (BS) is positioned to direct a first portion of a beam of electromagnetic radiation from said source (LS) thereof normal onto said sample (S) and a second portion thereof toward said first mirror (M31) which reflects it onto said sample (S) at an oblique angle such that it impinges thereupon at substantially the same location at which the first portion of said beam impinges. Said first portion of said beam, after normally reflecting from said sample (S) is directed back along the path of its incidence, through said beam splitter (BS) and normally toward said sample and after reflection therefrom toward said alignment detector (QD33). Said second portion of said beam, after obliquely reflecting from said sample (S), is directed to reflect from said second mirror (M32) toward said alignment detector (QD33). Said first chopper (CHP1) is in the pathway of said beam which passes through said beam splitter (BS) toward said alignment detector (QD33), and said second chopper (CHP2) is in the pathway of said beam which passes through the beam splitter (BS) toward the first mirror (M31), and after being directed thereby to obliquely reflect from said sample (S), being directed to reflect from said second mirror (M32) toward said alignment detector (QD33). In use said choppers (CHP1) and (CHP2) are operated at different frequencies which are distinguishable by the alignment detector (QD33).

It is noted that the choppers (CHP1) and (CHP2) can be placed in any functional location in the relevant beam path way.

Figure 4:
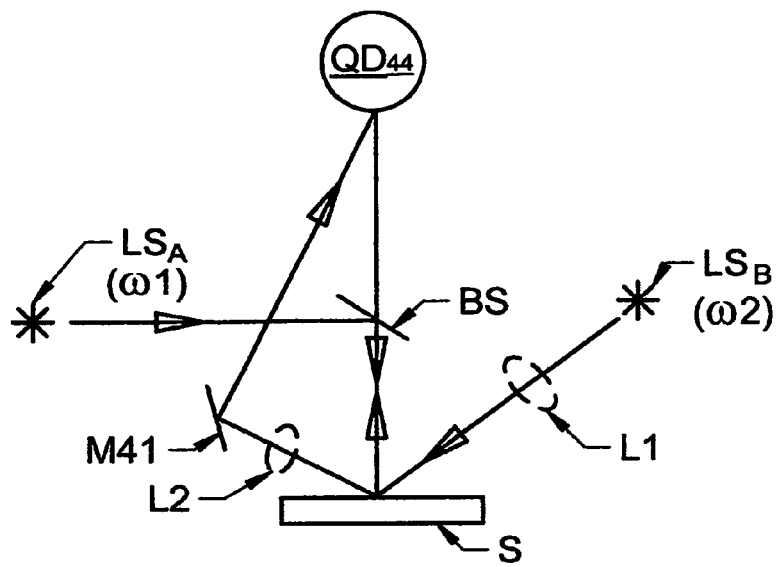
FIG. 4 shows a forth embodiment of a disclosed invention sample alignment system.

Turning now to FIG. 4, a forth sample alignment system embodiment comprises:
a) first (LSa) and second (LSb) source of electromagnetic radiation;
b) a beam splitter (BS);
c) at least a first (M41) mirror;
d) an alignment detector (QD44);
f) a stage for supporting a sample (S).

Said beam splitter (BS) is positioned to direct a portion of a beam of electromagnetic radiation from said first source (LSa) thereof normal onto said sample (S). Said portion of said beam, after normally reflecting from said sample (S) is directed back along the path of its incidence, through said beam splitter (BS) and toward said alignment detector (QD44). Said second source provides a beam of electromagnetic radiation which is directed to impinge on said sample (S) at an oblique angle such that it impinges thereupon at substantially the same location at which the first beam impinged, and after obliquely reflecting from said sample (S), is directed to reflect by said second mirror (M41) toward said alignment detector (QD44). Said first (LSa) and second (LSb) sources can produce electromagnetic radiation of different wavelengths and/or of different chopping frequencies which are separately distinguishable by the alignment detector (QD44).

Figure 5:
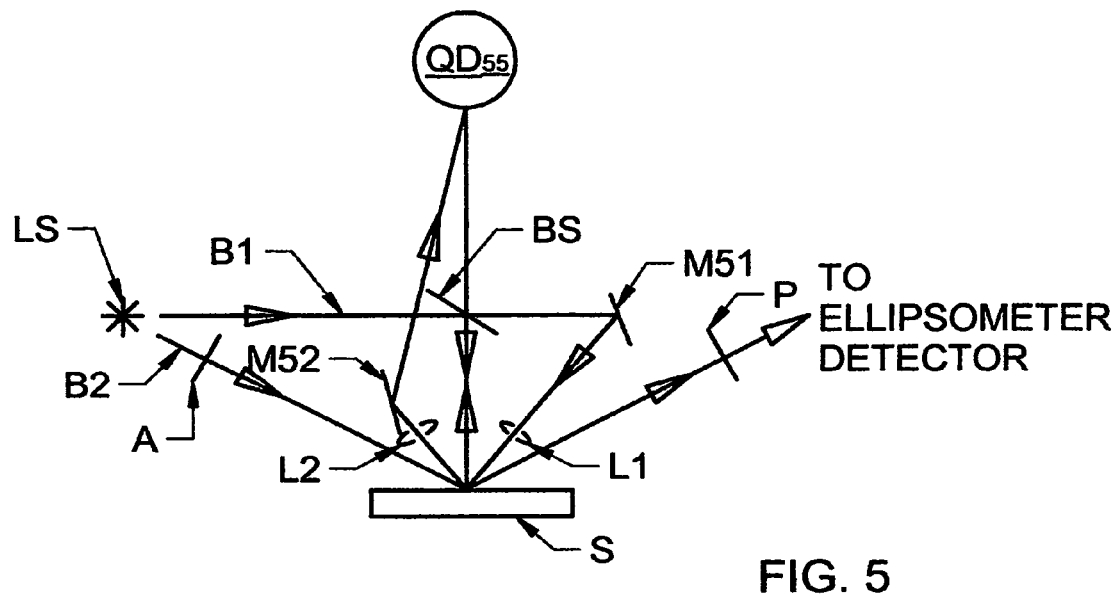
FIG. 5 shows a fifth embodiment of a disclosed invention sample alignment system.

FIG. 5 shows that a common source (LS) can be applied to provide both an ellipsometer beam and an alignment beam. This directly distinguishes over the Abraham U.S. Pat. No. 6,091,499 Patent and it is noted that use of the same source of electromagnetic radiation for both alignment and sample analysis avoids the problem of the alignment beam being of a wavelength which does not reflect from the sample. The same wavelengths are used in alignment as are used in ellipsometric sample analysis. Said system for orienting a sample on a stage in an ellipsometer system comprises a light source (LS), a polarizer (P), said stage, an analyzer (A) and a detector;
said system further comprises an alignment detection system with means for receiving input from said ellipsometer light source (LS), wherein said alignment detection system can detect both a tilt of a sample placed onto said stage, and a distance of said sample from said ellipsometer; and
said system further comprising an adjusting device, wherein said adjusting device can adjust tilt of said stage, and wherein said adjusting device can adjust the relative position of said ellipsometer and alignment detection system with respect to said stage.

The alignment detection system is to be considered as including embodiments shown in FIGS. 3 and 4, and can further comprise two alignment detectors (QS1) (QD2) as indicated in FIG. 1 for receiving tilt and distance information, instead of the single detector (QD55) as shown.

It is noted that the system alignment detection system can be locked into position relative to said ellipsometer by at least one selection from the group consisting of:
electronic; and
mechanical;

so that said stage can be adjusted with respect to said ellipsometer and said alignment detection system considered as one unit. (Note that physically, the ellipsometer and alignment system can be locked into a fixed relative position with respect to one another, or changing electronic alignment signals can be applied to effect adjusting device operation to maintain a functionally fixed relationship therebetween).

In any of the foregoing sample alignment systems the alignment detector can be a multi-element detector, (eg. a Quad Detector), or can be a detector which comprises a two dimensional plurality of detection elements arranged in an array.

The systems just disclosed can be beneficially applied in ellipsometer systems which sequentially comprise a source of a beam of electromagnetic radiation, polarizer means for imposing a state of polarization on said beam, a stage for supporting a sample, analyzer means for selecting polarization states of a beam of electromagnetic radiation after it interacts with a sample placed on said stage, and an ellipsometer detector.

It is further noted that the disclosed invention systems can be conveniently applied in automatic means for aligning the sample, wherein signals from the appropriate alignment or data detector(s) are used to control the vertical position and tilt of a sample.

It is also noted that where choppers are used, an ellipsometer arranged to provide a beam to the sample can be operated in ambient light instead of in a darkened environment. This can be an advantage in convenience.

Figure 6A:
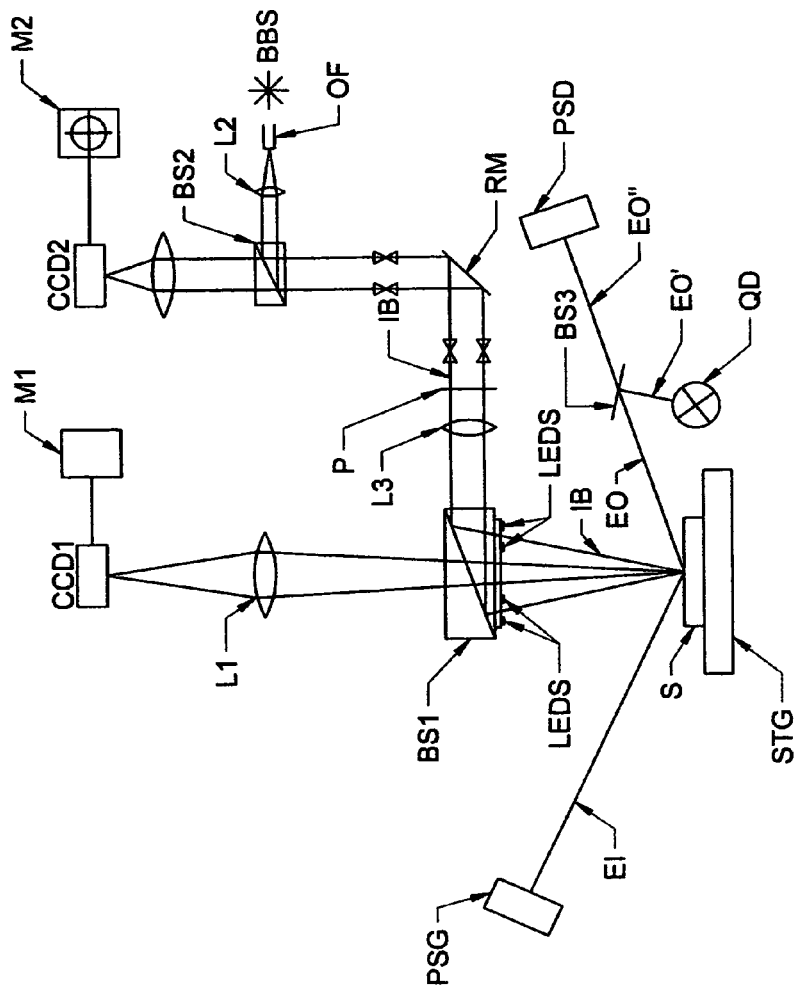
FIG. 6a is included to show a system suited to practicing a similar purpose as is the present invention, and which is Claimed in other Applications by the same Inventor herein.
Figure 6B:
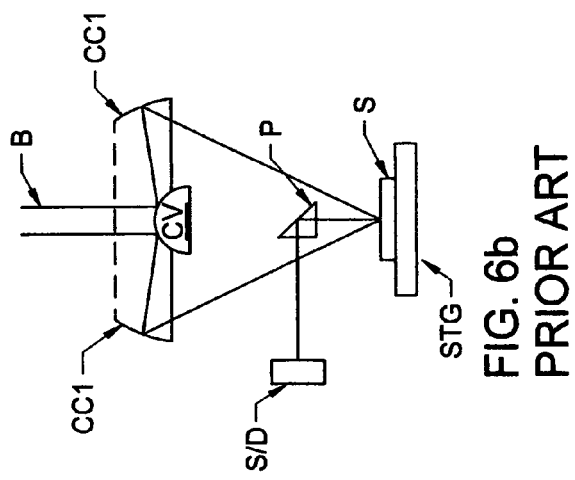
FIG. 6b shows a prior art approach to providing a vertically oriented beam to a sample.

For comparison, FIG. 6a is included to show a system suited to practicing a similar purpose as Claimed in other Applications by the same Inventor herein, and FIG. 6b shows a prior art approach to providing a vertically oriented electromagnetic beam onto a sample. FIG. 6a shows a Source (BBS) which provides an alignment beam (IB) to the surface of a Sample (S) along an essentially perpendicular locus via a Lens (L) a Beam Splitter (BS2), and Reflecting means (RM), Lens (L3) and Beam Splitter (BS1). The reflected beam makes its way back along the sequence of elements just recited but proceeds through Beam Splitter (BS2) and into Camera (CCD2) which provides signal to Monitor (M2). Sample (S) tip/tilt can be adjusted by observing Monitor (M2). The Camera (CCD1), via Monitor (M1) provides a visual indication of the Sample (S) as lit by Light Source (LEDS) positioned under the Beam Splitter (BS1). The FIG. 6a system shows a Quad Detector (QD) positioned to intercept a portion of a Beam (EO') of electromagnetic radiation provided by an Ellipsometer Polarization State Generator (PSG) as Beam (EI), via Beam Splitter (BS3) after is reflects from the Sample (S) and proceeds otherwise to Polarization Stage Detector (PSD) as Beam (EO"). In use, signals from the Quad Detector (QD) indicate the relative vertical positioning of a Sample (S) surface, the tilt/tip of which is adjusted by use of Beam (IB) as described. The FIG. 6a system can be applied in the system of the present invention. In addition, it should be appreciated that the Stage (STG) can be fitted with Actuators (ACT), which are provided signals from effective Alignment Detectors (ie. (CCD2) and (QD)), and which respond thereto by automatically adjusting Sample (S) tip/tilt and vertical height in a feedback loop.

Figure 6C:
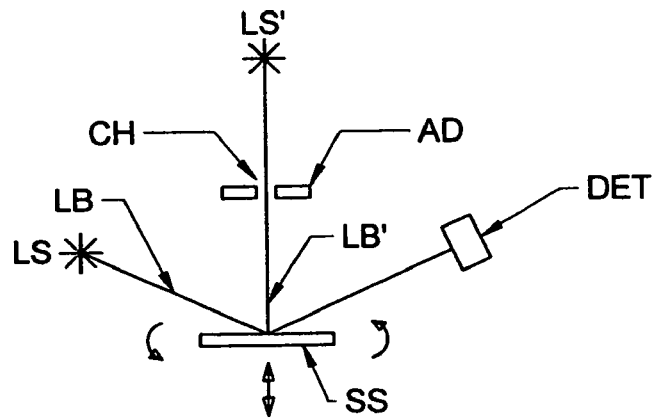
FIG. 6c shows a system which can be applied to provide a signal allowing "X" and "Y" plane adjustment.
Figure 7A:
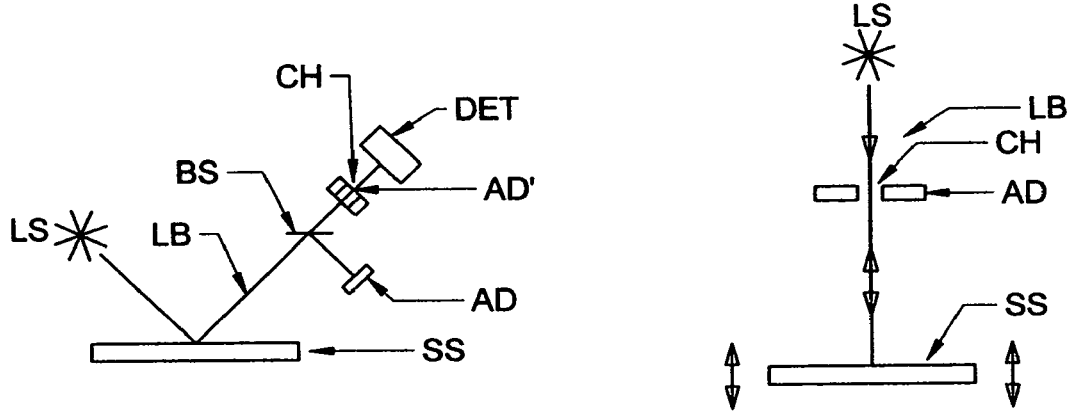
FIG. 7a shows a system which can be applied to provide a signal allowing "Z" distance adjustment.
Figure 7B:
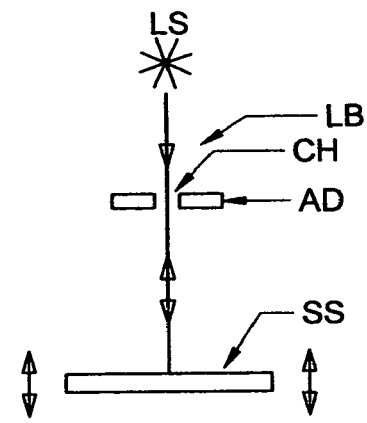
FIG. 7b shows a system which can be applied to provide a signal allowing "X"-"Y" tip/tilt adjustment.

FIG. 6c shows a configuration of an Alignment Detector which provides sensitivity to Sample Rotations, but not Vertical Height. FIG. 7a shows a configuration of an Alignment Detector (AD) which provides sensitivity to Sample Vertical Height. (Note that the Central Hole (CH) in the FIG. 5 Alignment Detector, and in the Alignment Detector (AD') in FIG. 7a need not be present in the FIG. 7a (AD) embodiment as electromagnetic radiation need not pass therethrough, but rather is reflected thereonto. FIG. 7b shows a system which can be applied to provide a signal allowing "X"-"Y" tip/tilt adjustment. When an electromagnetic beam, (LB) is directed to proceed downward, and reflect from the surface of the Sample (SS) directly back upward, it will pass through the Central Hole (CH) in both directions. If the Alignment Detector (AD) comprises multiple detector elements distributed circumferentially about said Central Hole (CH), when signals from each are zero or approximately equal, the Sample (SS) will be properly aligned in "X"-"Y" tip/tilt directions. (Note, the signals from the multiple detector elements need not be equal, but can be reference values which are associated with proper alignment.

Figure 6D:
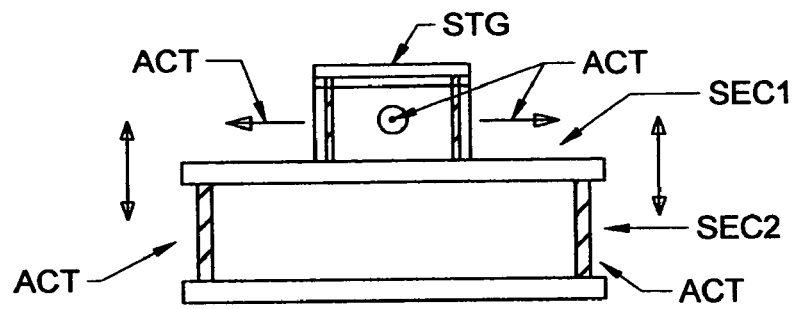
FIG. 6d shows that the Stage (STG) for supporting a sample can be comprised of two Sections.

FIG. 6d shows that the Stage (STG) for supporting a sample is comprised of two Sections, the First Section (SEC1) being comprised of means for adjusting a sample location in two dimensions, and the Second Section (SEC2) being comprised of means for moving the first section in a height and tip/tilt dimension. In use the First Section (SEC1) is adjusted, such that a desired location of a surface of a sample placed on said Stage (STG) moves in a plane which is parallel to that of a plane formed by the two dimensions in which First Section (SEC1), movement is possible, (ie. to the left and right or in and out of the paper), said positioning being locked-in once achieved. The Second Section (SEC2) is applied to orient a surface of a sample placed on the First Section (SEC1) with respect to an Ellipsometer Beam, (see (LB) in FIG. 6c for instance), perhaps by adjusting screws at the corners of the Second Section (SEC2). The result is that the Second Section (SEC2) allows adjustment of the "Z" height of a surface of a sample and the tip/tilt orientation of the plane in which said first section causes movement of said sample. In use the plane in which the First Section (SEC1) causes the surface of a sample to move with respect to an electromagnetic beam (LB), provides that the plane of incidence which includes both a perpendicular to the sample surface and the locus of said electromagnetic beam projects perpendicular to the sample surface.

Figure 6E:
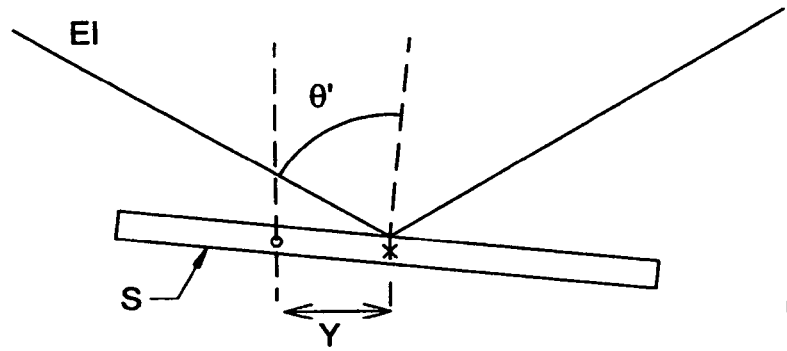
FIGS. 6ea-6ec shows a translational effect caused by tipping a sample.
Figure 6E:
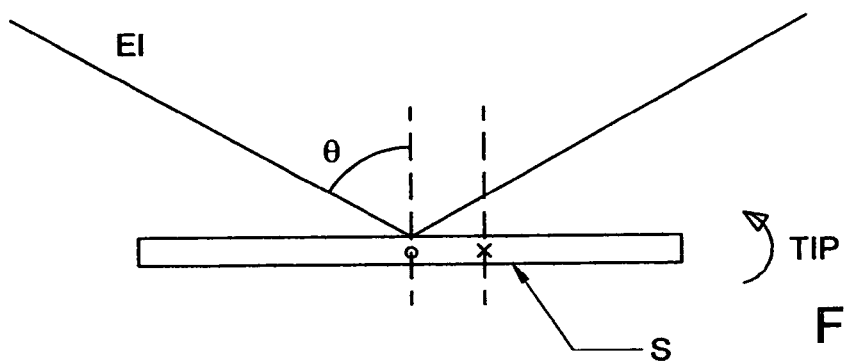
Figure 6E:
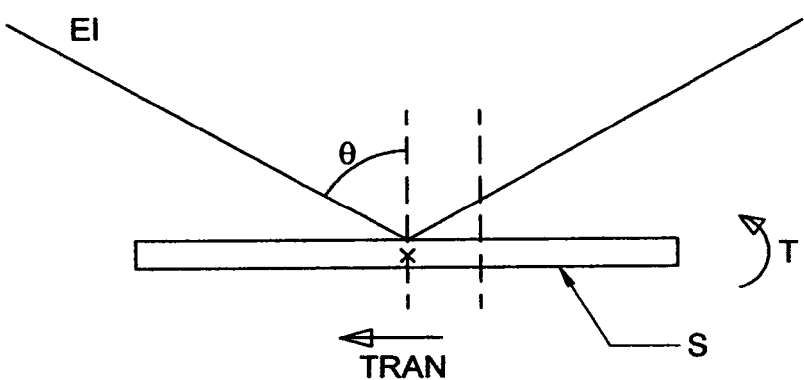
Figure 6E:

FIGS. 6ea-6ec are included to demonstrate a translational effect of tipping a sample, regarding the spot on a sample (S) where an oblique angle-of-incidence (O') beam reflects therefrom. Note in FIG. 6ea that the incident Beam (EI) approaches the Sample (S) and reflects from Spot (x) on the surface thereof. FIG. 6eb shows the Sample (S) tipped (TIP) to orient the normal to the surface of the sample vertically so that the angle-of-incidence is (O), and that the incident Beam (EI) reflects from a spot removed from the original Spot (x). FIG. 6ec shows that a translation (TRAN) of the Sample (S) is necessary to place Spot (x) so that incident Beam (EI) again reflects therefrom. A preferred embodiment of the present invention includes automated actuator means for effecting a coordinated translation when a tipping of a sample is effected. Note that an actual application of the demonstrated effect will typically not involve an entire Sample (S) being at an angle (O'), but rather will involve a Sample (S) with an irregular surface as demonstrated in FIG. 6ed, wherein a Spot to be investigated does not have a vertically projecting normal without an effected tipping thereof.

It should be appreciated that signals developed by Adjustment Detectors (AD) (AD') can be fed to Actuators which are applied to a Stage, such as demonstrated in FIG. 6d, to automatically position a sample, (in "X", "Y" and "Z" directions), and to adjust sample tip/tilt thereof. The actuators can be demonstratively visualized as any means for causing movement to the left/right and in/out and up/down on the page as regards the First Section (SEC1), and for adjusting sample (SS) tip/tilt via the Second Section (SEC2).

Figure 8:
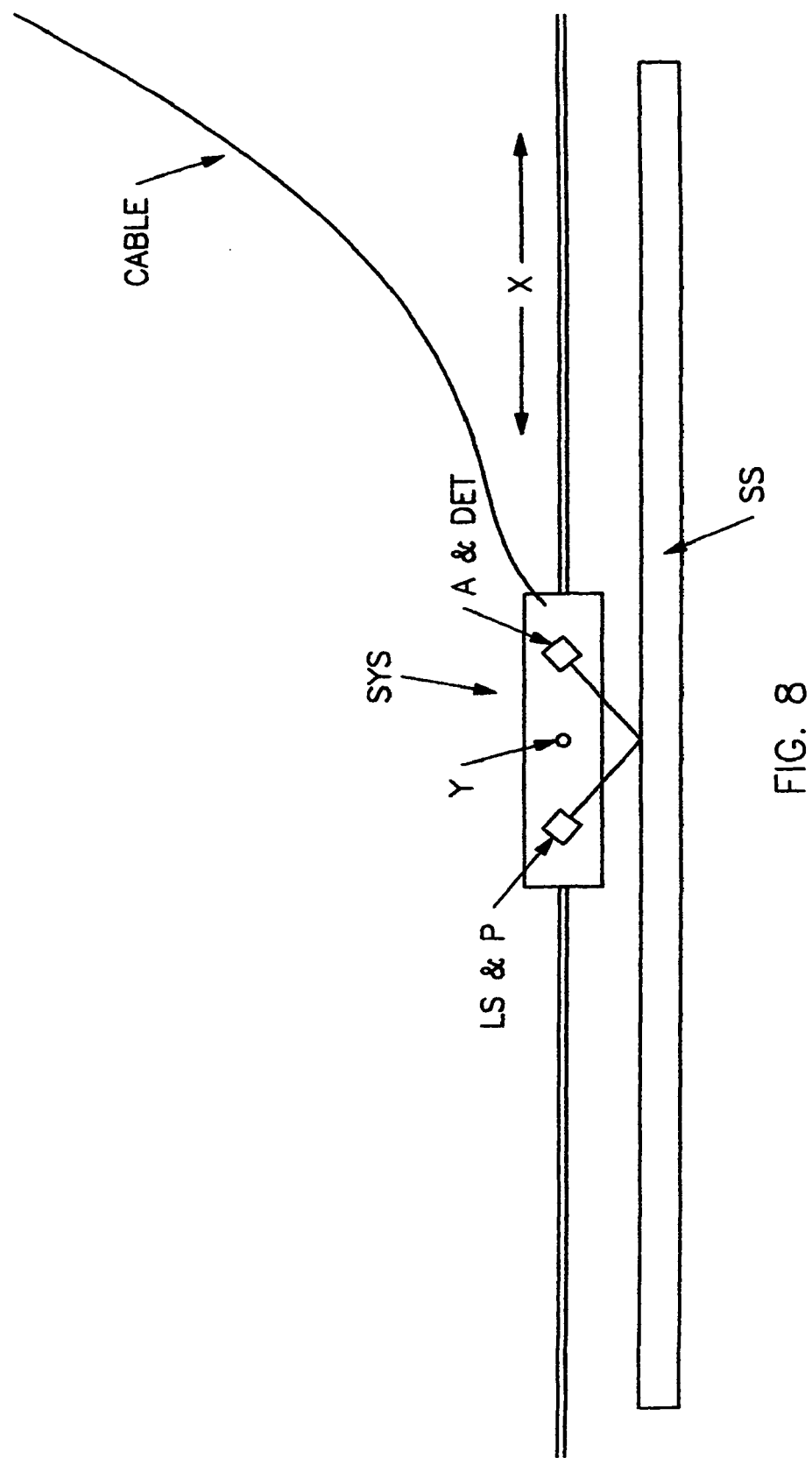
FIG. 8 shows demonstrates a present invention ellipsometer system situated on "X"-"Y" control means above a large sample.
Figure 9:
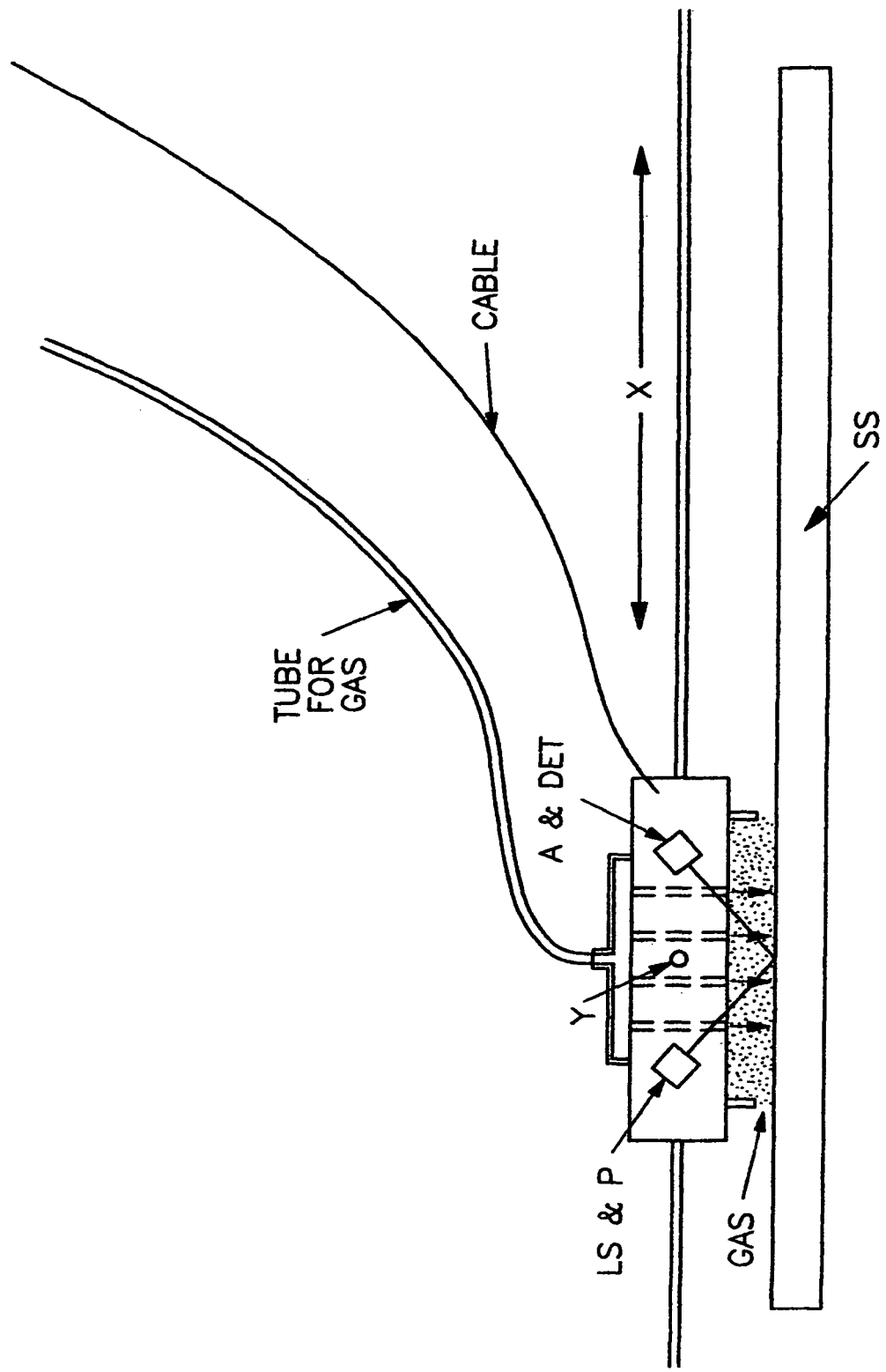
FIG. 9 demonstrates a present invention ellipsometer system situated on "X"-"Y" control means above a large sample, including a system for flowing purging gas onto a sample.

FIGS. 8 and 9 are presented as the scope of the present invention includes use of ellipsometers which can be moved with respect to a stationary sample. FIG. 8 shows demonstrates a present invention ellipsometer system (SYS) situated on "X"-"Y" control means above a large sample (S). Indicated in block form are (LS) and (P), and (A) and (DET). A Cable is shown which can be used to provide power to, and transmit data from the ellipsometer system (SYS). FIG. 9 is similar to FIG. 8, but has means added for flowing purging gas onto a sample at the point it is being investigated, during a period in which UV and IR wavelength Electromagnetism interacts therewith. As regards FIGS. 8 and 9, in use the system selected from the group consisting of:

reflectometer;
rotating analyzer ellipsometer;
rotating polarizer ellipsometer;
rotating compensator ellipsometer;
modulation element ellipsometer;
Mueller Matrix measuring system;

can be thought of as "flying" over the sample.

Figure 15:
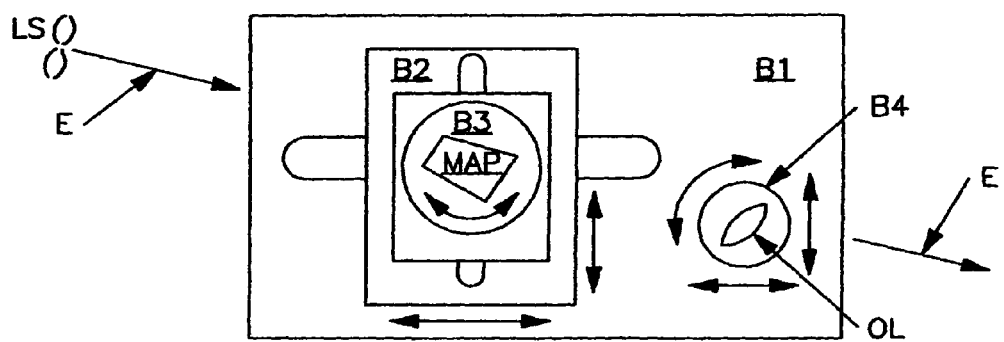
FIG. 15 shows a side elevational view of an adjustable mounting means for a Multiangle Prism (MAP), and optionally an Optical Lens (OL).
Figure 16:
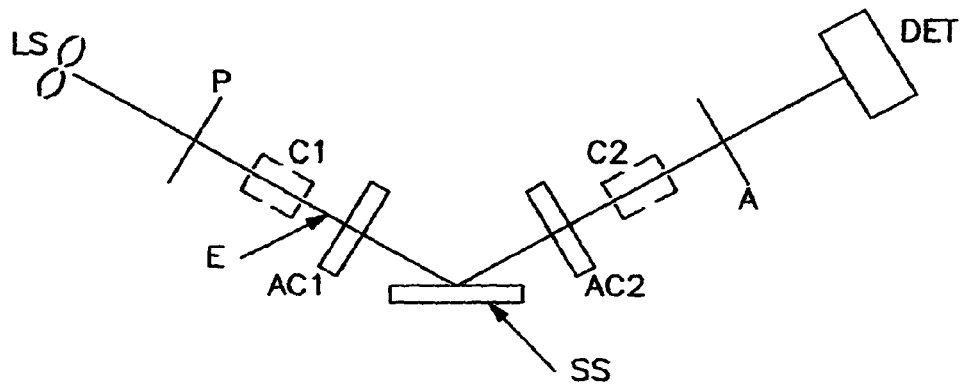
FIG. 16 shows a more detailed presentation of an ellipsometer system to which the Present Invention is applied.
Figure 17A:
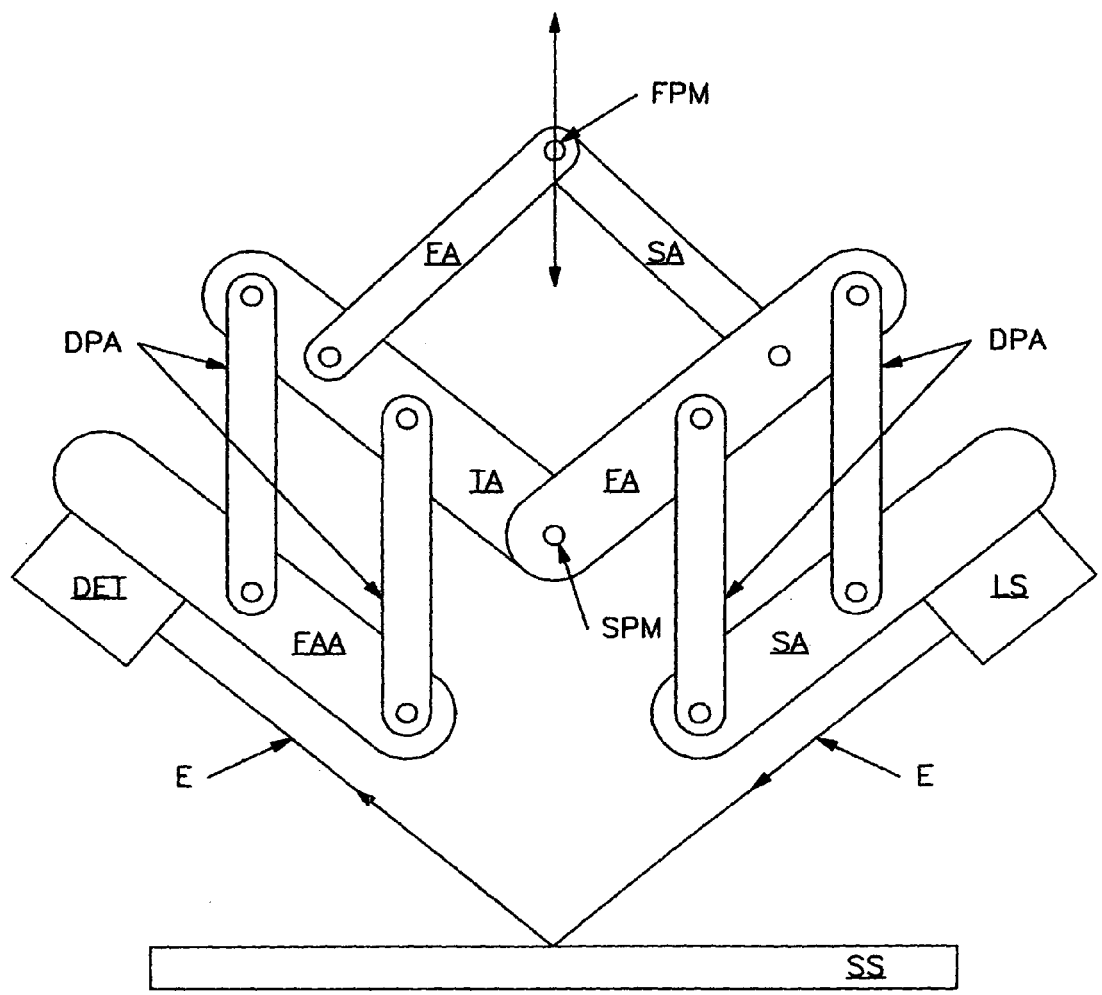
FIG. 17a shows an approach to mounting Ellipsometer Polarization State Generator and Polarization State Analyzer Systems which allow easily changing the Angle-Of-Incidence of a Beam of Electromagnetic radiation caused to impinge on a Sample, as well as easily change the vertical height of thereof above the Sample.
Figure 17B:
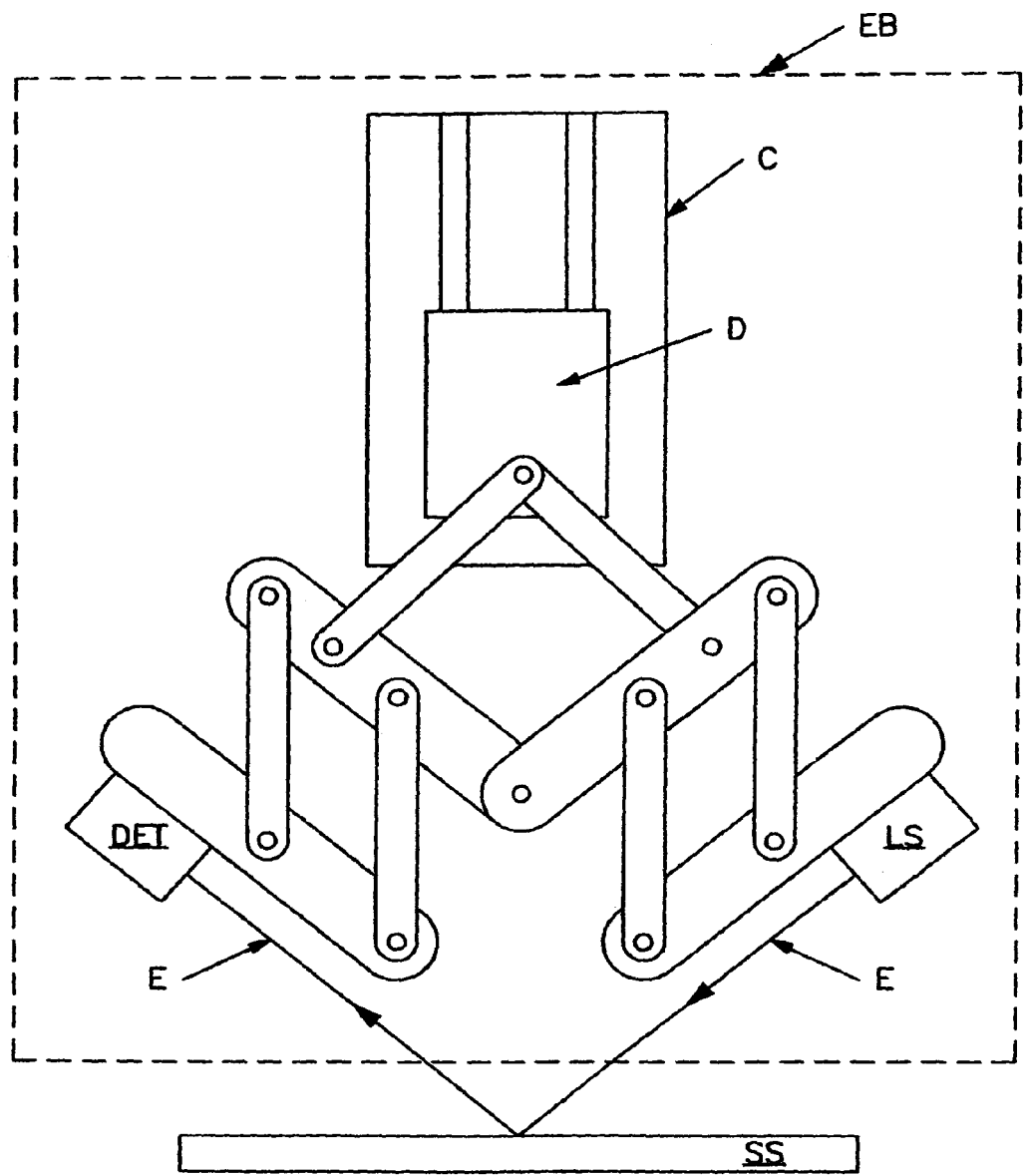

Continuing, FIGS. 10-16 describe Angle-of-Incidence changing systems and FIGS. 17*a* and 17*b* demonstrate an alternative system for achieving a similar effect.

Figure 10:
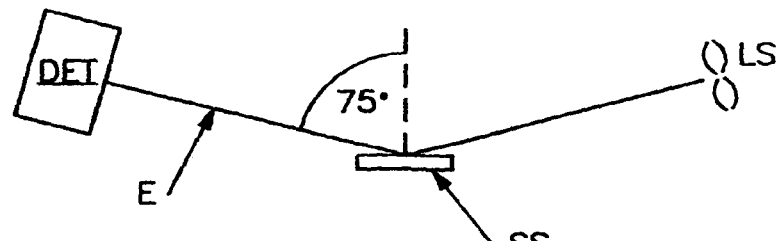
FIG. 10 shows a Front View of a Conventional Ellipsometer, Polarimeter or Reflectometer System with an Electromagnetic Beam shown approaching and reflecting from a sample system at an (AOI) of, for instance, 75 degrees.
Figure 11:
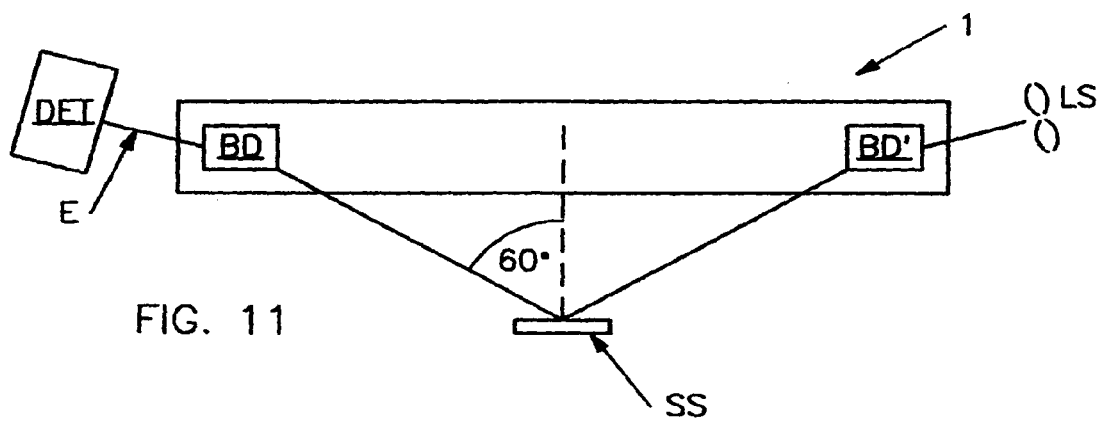
FIG. 11 shows that the (AOI) is changed to, for instance, 60 degrees when a Present Invention System (1) is placed in the pathway of the Electromagnetic Beam.
Figure 12A:
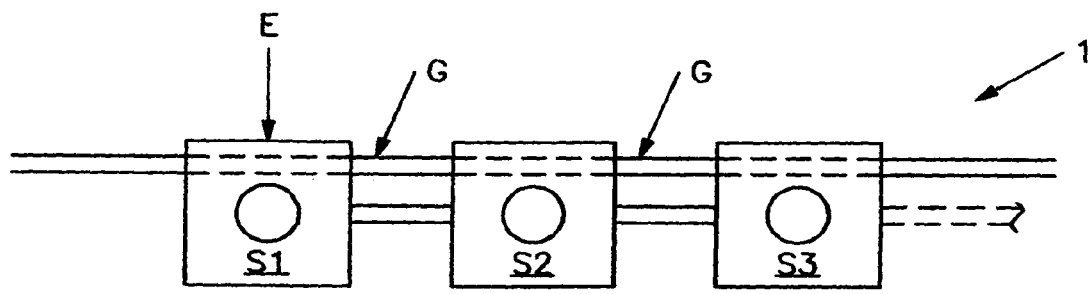
FIG. 12a shows a Side View of Present Invention System(s) (S1) (S2) (S3) mounted on a Guide (G) upon which they can be slid right and left. Present Invention System (S1) is shown slid into position to intercept Electromagnetic Beam (E).
Figure 12B:
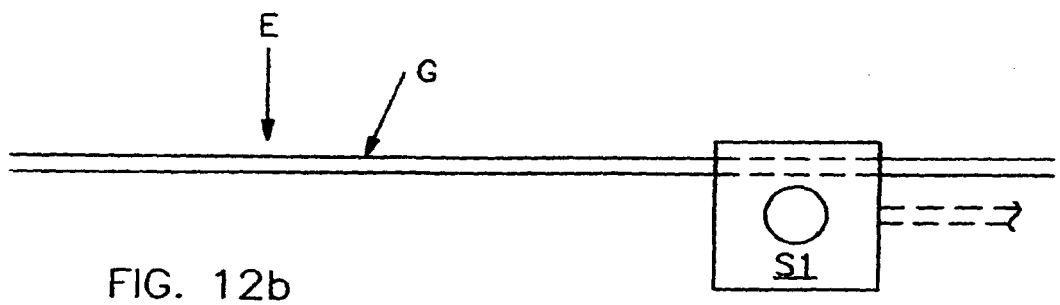
FIG. 12b shows a Side View of the system shown in FIG. 3a with Present Invention System(s) (S1) (S2) (S3) slid to the right therein such that none thereof intercepts Electromagnetic Beam (E).

FIG. 10 shows a Front View of a Material System Investigating System, (eg. Ellipsometer, Polarimeter, Reflectometer or Spectrophotometer System), with an Electromagnetic Beam shown approaching and reflecting from a Sample System (SS) at an (AOI) of, for instance, 75 degrees with respect to normal. FIG. 11 shows that the (AOI) is changed to, for instance, 60 degrees with respect to normal when a disclosed invention electromagnetic beam intercepting angle-of-incidence changing system (1) is placed in the pathway of the Electromagnetic Beam. FIG. 12*a* shows a Side View of a disclosed invention electromagnetic beam intercepting angle-of-incidence changing system mounted on a Guide (G) upon which they can be slid right and left. The location of a Materials System Investigating System with respect to the disclosed invention electromagnetic beam (E) intercepting angle-of-incidence changing system is indicated by (E), which is the same (E) indicated in FIGS. 10 and 11. Referral to FIGS. 12*a* and 12*b* shows that a sliding motion to the left will place a disclosed invention electromagnetic beam intercepting angle-of-incidence changing system (S1) (S2) (S3) in the pathway of an Ellipsometer System Electromagnetic Beam (E), (see FIG. 12*a*), and sliding disclosed invention electromagnetic beam intercepting angle-of-incidence changing system to the right moves them out of the Electromagnetic Beam, (see FIG. 12*b*). (Note right and left in FIGS. 12*a* and 12*b* correspond to a perpendicular to the plane of the surface of the paper in FIGS. 10 and 2.

Figure 13:
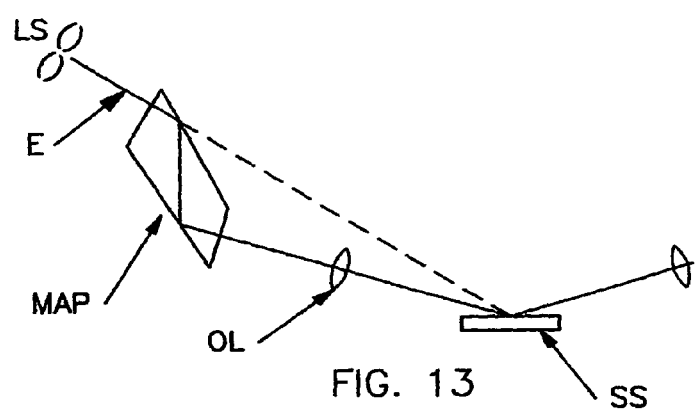
FIG. 13 shows Multiangle Prisms (MAP) comprise a disclosed invention electromagnetic beam intercepting angle-of-incidence changing system on right and left sides thereof.
Figure 14A:
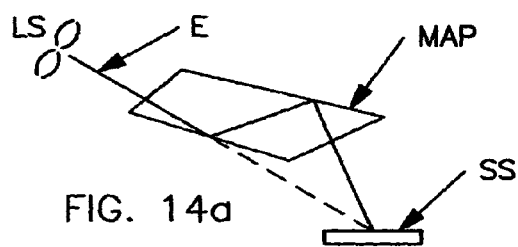
FIG. 14a shows how a Multiangle Prism (MAP) changes the pathway of an Electromagnetic Beam by Total Internal Reflection therewithin.
Figure 14B:
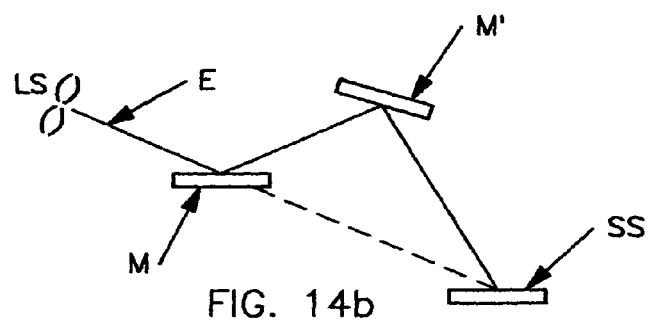
FIG. 14b shows how a plurality of Mirrors can change the pathway of an Electromagnetic Beam by Reflection therefrom.

FIG. 13 shows a Multiangle Prism (MAP) in a disclosed invention Electromagnetic Beam (E) intercepting Angle-of-Incidence changing system (1), on the left side thereof, (as indicated (BD) in FIG. 12). Note that the orientation of the (MAP) increases the (AOI) in FIG. 13, whereas in FIGS. 12, (and 14*a*), the (MAP) is oriented to decrease the (AOI). FIG. 14*a* shows how a Multiangle Prism (MAP) changes the pathway of an Electromagnetic Beam by Total Internal Reflection therewithin. The shapes and materials which characterize the prisms can be designed and selected to cause the (desired (AOI) change, as well as effect phase shifts entered by total internal reflections to be stable, or at least have small sensitivity to changes in (AOI). Polymer for Far IR, Silicon or Germanium for IR, and Quartz for UV, VIS-NIR or CaF for VUV, for instance, can be utilized. And note that a two or more Multiangle Prisms can be present on at least one side of the sample system, to provide an (AOI) not possible where only one is present. FIG. 14*b* shows a plurality of mirrors (M) (M') can also form disclosed invention electromagnetic beam intercepting angle-of-incidence changing system. FIG. 13 also shows Optional Lenses (OL) can be positioned to focus a beam of electromagnetic radiation onto a spot on a sample system. Said Optional Lenses (OL) can be independently mounted, or affixed to the Multiangle Prisms (MAP). Note, it is possible to have two "Present Invention Systems" which provide the same AOI, one having Optional Lenses for focusing present, and the other not.

Figure 14C:
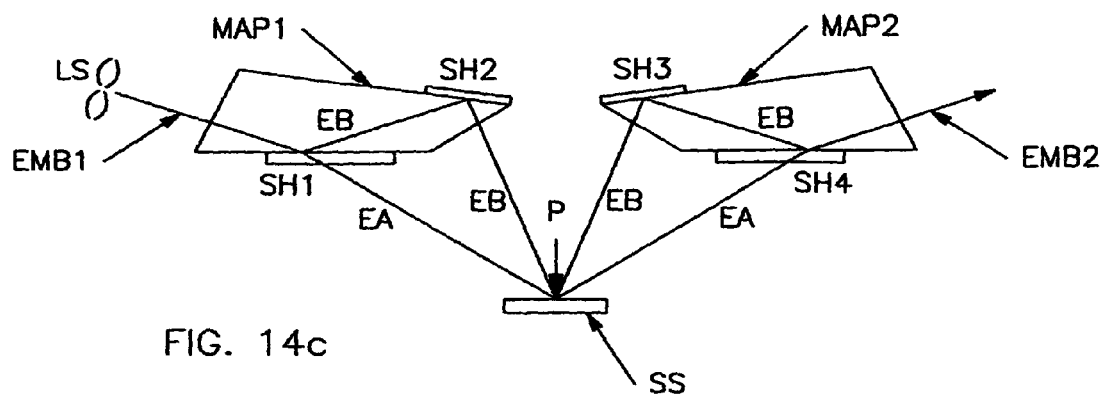
FIG. 14c shows additional configurations of Multiple Angle Prisms (MAP1) and (MAP2) which have Shutters (SH1) & (SH2), and (SH3) & (SH4) respectively present thereupon.
Figure 14D:
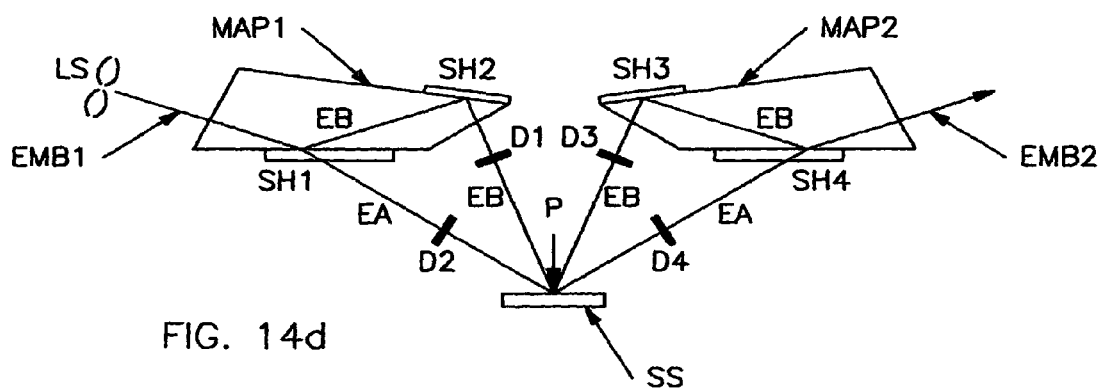
FIG. 14d shows FIG. 14c with door shutters (D1), (D2), (D3) and (D4) present therein.

FIGS. 14*c* and 14*d* show additional configurations of Multiple Angle Prisms (MAP1) and (MAP2) which have Shutters (SH1) & (SH2), and (SH3) & (SH4) respectively present thereupon. Said Shutters (SH1) & (SH2), and (SH3) & (SH4) can be, for instance, voltage controlled liquid crystals or electromagnetic-optics means for effectively changing the refractive index of the top and bottom surfaces of a multi-angle prism, for the purpose of controlling the internal reflection/transmission properties. FIG. 14*c* shows Input Electromagnetic Beam (EMB1) entering Multi-Angle Prism (MAP1) and interacting with the interface between said Multi-Angle Prism (MAP1) and said Shutter (SH1). If said interface is substantially transmissive then Beam (EA) proceeds to the Sample System, and reflects therefrom at point (P). Said Beam (EA) then proceeds through Multi-Angle Prism (MAP2) and exits therefrom as Output Electromagnetic Beam (EMB2). If, however, the interface between said Multi-Angle Prism (MAP1) and said Shutter (SH1) is substantially reflective, it should be appreciated that Input Electromagnetic Beam (EMB1) will reflect thereat and become beam (EB). It is to be assumed that the interface between said Multi-Angle Prism (MAP1) and said Shutter (SH1) is also substantially reflective, so that beam (EB continues to reflect from Sample System, and reflects therefrom at point (P), and continue through Multi-Angle Prism (MAP2), wherein it interacts with reflective interfaces between said Multi-Angle Prism (MAP1) and said Shutters (SH3) & (SH4) to emerge as Output Electromagnetic Beam (EMB2).

FIG. 14*d* shows FIG. 14*c* with additional Physical Door-Shutter means (D1), (D2), (D3) and (D4) in place to further enhance the Transmission/Reflection effect described with respect to FIG. 14*c*. For instance, when the interface between Multi-Angle Prism (MAP1) and said Shutter (SH1) is substantially transmissive, Physical Door-Shutter (D2) will be open and Physical Door-Shutter (D1) will be closed. The operation of Said Physical Door-Shutter means (D1), (D2), (D3) and (D4) must, of course, be coordinated with operation of Shutters (SH1) & (SH2), and (SH3) & (SH4), but when present serve to essentially completely overcome the effect of any imperfect operation of Shutters (SH1) & (SH2), and (SH3) & (SH4).

Figure 14E:
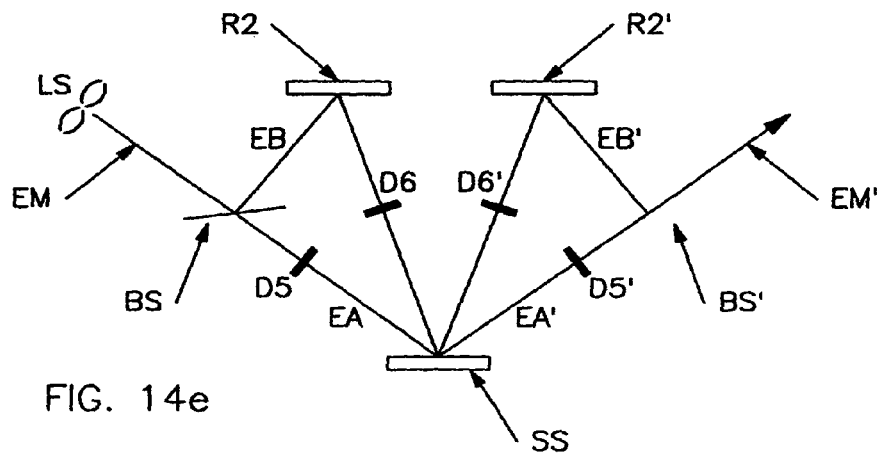
FIG. 14e shows a system for providing multiple angles-of-incidence utilizing Beam Splitter, Reflective means and shutter doors.
Figure 14F:
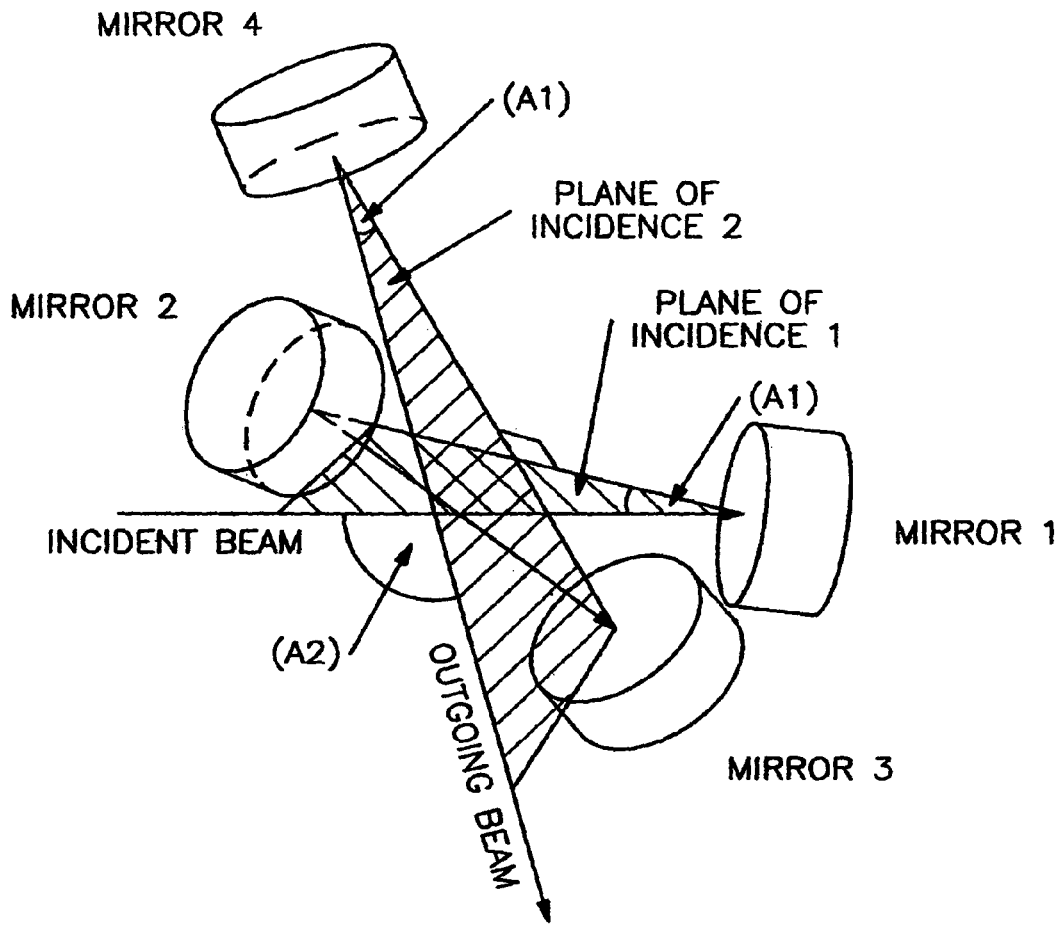
FIG. 14f system is, however, identified as a particularly relevant way to use reflective means to alter the trajectory of a Beam of electromagnetic Radiation, without significantly changing the phase angle between orthogonal components thereof.

FIG. 14*e* shows an alternative system for effecting different angles of incidence. Note that a Beam Splitter (BS) receives a Beam of Electromagnetic Radiation (EM) and continuously reflects approximately half (EB) and transmits (EA) the remainder. The reflected portion (EB') reflects from a Second Reflection means (R2). Both the reflected (EB') and Transmitted (EA) Electromagnetic Beams arrive at the same point on Sample System (SS), but at different angles-of-incidence. Note, importantly, that Door Shutters (D5) and (D6) are present, and are operated to block one or the other of (EA) and (EB') when desired. After the Sample System (SS), whether it is electromagnetic beam (EA) or (EB') which is allowed to proceed, note that it makes its way to the Detector (DET) by a pathway which is a mirror image to that which brought it to the Sample System (SS) from the Electromagnetic Beam Source. Note that typically four shutter doors (D5) (D6) (D5') (D6') are be present, two on each side of the sample system (SS), said shutter doors being positioned in the loci of the electromagnetic beams which transmit through (EA) and reflect from (EB') the beam splitter (BS) on the incident side of the means for supporting a sample system (SS).

It is important to mention U.S. Pat. No. 5,969,818 to Johs et al. which is incorporated hereinto by reference. Said 818 Patent describes a Beam Folding Optics System which serves to direct an electromagnetic beam via multiple reflections, without significantly changing the phase angle between orthogonal components therein. Briefly, two pairs of mirrors are oriented to form two orthogonally related planes such that the phase shift entered to an electromagnetic beam by interaction with the first pair of mirrors is canceled by interaction with the second pair. The Reflector (R2) in FIG. 14e, (and a similar Reflector in an output side) can comprise Patent 818 Beam Folding Optics. FIG. 5 from said 818 Patent is reproduced herein as FIG. 14f. Note that Beam (EB) in FIG. 14e is shown as is Beam ((EB'), and that Mirrors 1 and 2 form a First Pair, and Mirrors 3 and 4 a Second Pair. Note how the Planes of incidence 1 and 2 are orthogonally related to one another. It is not a focus of Patentability herein to specify any particular FIG. 14e Second Reflective Means (R2) system. The FIG. 14f system is, however, identified as a particularly relevant way to use reflective means to alter the trajectory of a Beam of Electromagnetic Radiation, without significantly changing the phase angle between orthogonal components thereof. Such an effect is similar to that provided by Total Internally Reflective Multi-Angle Prisms, as shown in FIGS. 13, 14a, 14c and 14d herein.

The disclosed invention system can also include means for adjusting, for instance, tilt, translation and rotation orientations of the multi-angle prisms and/or the Optional Lenses (OL) within the containing structure. Such presence facilitates easy system set-up optimization. FIG. 15 demonstrates mounting Bases (B1), (B2) and (B3) mounted with respect to one another so that mounting Base (2) can move right and left on mounting Base (1), and so that mounting Base (3) can rotate on mounting Base (2). A Multiangle Prism (MAP) is shown mounted to mounting Base (3). Mounting Base (1) can of course be mounted in a Present Invention Electromagnetic Beam (E) intercepting Angle-of-Incidence (AOI) changing system (1), as shown in FIG. 12, in the position of (BD) or (BD') in a manner to allow it Rotational or any Linear Degrees of Motion Freedom. In particular motion into and out of the plane of the paper is also possible at the (B1), (B2) and/or (B3) level, as required. Note that an Optical Lens (OL) is also shown rotatably and translatably mounted via mounting Base (B4) to mounting Base (1). This is an optional feature, and it is noted that the Optical Lens (OL) can be absent, or separately mounted. FIG. 15 is to be considered only demonstrative, and functional mountings can include any required translation, tilt and rotation adjustment capability shown, and not directly shown or visible in the view presented.

It is also to be appreciated that while an Electromagnetic Beam (E) which interacts with a Sample System (SS) will often be polarized, where the disclosed invention system (1) is used with a Reflectometer System, this need not be the case. Reflectometers which produce unpolarized electromagnetic radiation and cause impingement at oblique (AOI's), (instead or in addition thereto ellipsometer produced beams), can have the disclosed invention applied thereto as well.

FIG. 16 provides a general elemental configuration of an ellipsometer system (10) which can be applied to investigate a sample system (SS). Shown are, sequentially:
 a. a Source of a beam electromagnetic
  radiation (LS);
 b. a Polarizer element (P);
 c. optionally a compensator element (C1);
 d. (additional element(s)) (AC1);
 e. a sample system (SS);
 f. (additional element(s)) (AC2);
 g. optionally a compensator element (C2);
 h. an Analyzer element (A); and
 i. a Detector System (DET).

It is noted that the elements identified as (LS), (P) and (C1) can be considered to form, as a group, a Polarization State Generator (PSG), and the components (C2), (A) and (DET) can be considered, as a group, to form a Polarization State Detector (PSD). It is to be understood that the d. and f. "additional elements", (AC1) and (AC2), can be considered as being, for the purposes of the disclosed invention Disclosure, input and output electromagnetic beam intercepting angle-of-incidence changing system elements. (Note the presence of indication of an Electromagnetic Beam (E) in FIG. 16, which for orientation it is noted corresponds to the location shown in FIGS. 12, 12a and 12b).

Where, as is generally the case, input (AC1) and output (AC2) additional elements, (eg. multiangle prisms or functional equivalents as represented by (BD) and (BD') in FIG. 12), have bi-refringent characteristics, it must be appreciated that said characteristics must be accounted for in a mathematical model of the ellipsometer and sample system.

It is to be appreciated that single systems shown FIGS. 14c, 14d, 14e can be fixed in place and various shutters and door shutters operated to effect beam directing. However, multiple embodiments shown in said FIGS. 14c, 14d and 14e can be mounted to a slidable means to enable effecting any of a plurality of angles-of-incidence. Once in place however, two angles-of-incidence can be effected by a FIG. 14c, 14d or 14e system without physically moving it into an out of a beam of electromagnetic radiation.

It is beneficial at this point to refer to the paper by Johs, titled "Regression Calibration Method for Rotating Element Ellipsometers", which was referenced in the Background Section of this Disclosure. Said paper describes a mathematical regression based approach to calibrating rotating element ellipsometer systems. Said calibration procedure provides that data, (eg. ellipsometric ALPHA and ellipsometric BETA values), be obtained as a function of an ellipsometer system Polarizer Azimuth, as said Polarizer Azimuth is stepped through a range of angles, (eg. sixty (60) degrees to one-hundred-sixty (160) degrees). A mathematical model of the ellipsometer system and a sample system under investigation is provided, and a mathematical square error reducing technique is applied to evaluate parameters in said mathematical model. Successful calibration leads to experimental data and calculated data curves being essentially coincident.

Further insight to the benefit of applying 630 Patent-type regression calibration, and 777 Patent window-like effect corrections to ellipsometer and the like systems which include the disclosed invention multiple-AOI providing system, having then been illuminated herein, can be found in said 630 and 777 Patents which are incorporated by reference in this Specification. Said 777 Patent demonstrates that a methodology for correcting for affects of acquiring ellipsometric data through standard vacuum chamber windows, which can be applied to correcting affects of disclosed invention (AOI) changing systems, has been developed and tested. The key insight enabling said accomplishment is that bi-refringence can be split into "out-of-plane" and "in-plane" components, where the "plane" referred to is the plane of incidence of an electromagnetic beam of radiation with respect to a sample system. Splitting the electromagnetic beam into said orthogonal components allows derivation of second order corrections which were tractable while allowing an ellipsometer system calibration procedure to determine values of parameters. Again, said ellipsometer system calibration procedure allows parameter values in "out-of-plane" component retardation representing equations to be directly evaluated, with the "in-plane" component being an additive factor to a sample system DELTA. A separate step, utilizing a sample system for which retardance can be modeled by a parameterized equation, allows evaluation of the parameters in parametric equations for the "in-plane" components of windows separately. Work reported in the literature by other researchers provided equations which corrected only first order effects, and said equations have proven insufficient to correct for large, (eg. six (6) degrees), of retardation which is typical in standard vacuum chamber windows and which can occur in disclosed invention (AOI) changing systems. It is noted that each total internal reflection in a multiangle prism can impart up to about 45 degrees retardance, depending on the internal reflection angle. Four such bounces can then impart on the order of 160 degrees total phase retardance between the electromagnetic beam orthogonal components.

Continuing to use vacuum chamber windows as example, it is noted that said prior work orthogonal components were derived with respect to window fast axes, which is offset from the sample system plane of incidence). Where the window retardence becomes small, (eg. at longer wavelengths), parameter evaluation in equations for said orthogonal components becomes difficult, as it becomes difficult to determine fast axis orientation. This means that where fast axis orientation can not be identified, algorithm instability becomes a problem. Furthermore, the fast axis orientation of window retardance would also correlate with a sample system DELTA parameter unless a global regression fit using a parameterizable sample system is performed at calibration time. Said methodology comprising two steps as disclosed herein, fully and unambiguously determines correction terms in-situ.

After parameters in parameterized equations for retardance are evaluated by the method of the disclosed invention, ellipsometric data can be taken through disclosed invention (AOI) changing systems and said data can be quickly and accurately analyzed by applying the correction factors in a mathematical model for a sample system, (in the case where a Rotating Analyzer ellipsometer system was used to acquire data), or the (AOI) changing system effects can be simply quantitatively subtracted away to yield "true" ellipsometric PSI and DELTA values, (in the case where a Rotating Compensator ellipsometer system was used to acquire data). Finally, it is noted that the Patent to Johs et al. U.S. Pat. No. 6,034,777, provides demonstrative data obtained by practice of the described correction methodology as applied to other systems. Said data is incorporated by reference herein and should be considered as demonstrative of results obtained when it is applied to systems including disclosed invention (AOI) changing systems.

It is noted that shutters (SH1) (SH2) (SH3) (SH4) and shutter doors (D1) (D2) (D3) (D4) (D5) (D6) (D5') (D6') can be of any functional type, such as mechanical or voltage driven liquid crystal devices.

Finally, FIGS. 17a and 17b show a mechanical system for mounting a Reflectometer or Spectrophotometer Source and Detector, or Ellipsometer or Polarimeter Polarization State Generator, (eg. Source, Polarizer and optionally compensator), and Polarization State Analyzer, (eg. optional Compensator, Analyzer and Detector), Systems. Said approach to mounting allows easily changing the Angle-Of-Incidence of a Beam of Electromagnetic radiation caused to impinge on a Sample. Said system for setting the angle of incidence of a beam (E) of electromagnetic radiation comprises, as viewed in elevation, First (FA) and Second (SA) arms pivotally interconnected to one another at an upper aspect thereof by a First Pivot Means (FPM), said first (FA) and second (SA) arms projecting downward and to the left and right of said First Pivot Means (FPM); distal ends of said First (FA) and Second (SA) arms being pivotally affixed to Third (TA) and Forth (FA) arms, said Third (TA) and Forth (FA) arms being pivotally interconnected to one another by Second Pivot Means (SPM) at a lower aspect thereof, said Third (TA) and Forth (FA) arms being projected upward and to the left and right of said Second Pivot Means (SPM) at said lower aspect thereof; there being at least two pivotally affixed substantially Downward Projecting Arms (DPA) to each of said Third (TA) and Forth (FA) arms, distal ends of which are pivotally affixed to Fifth (FAA) and sixth (SA) arms which are not interconnected to one another, but project upward to the left and right, respectively. There are affixed to one of said Fifth (FAA) and Sixth (SA) arms a Source (LS) of a beam of electromagnetic radiation, and to the other of said Sixth (SA) and Fifth (FAA) arms a Detector (DET) of said Beam (E) of electromagnetic radiation. There is further a Sample (SS) located such that a Beam (E) of electromagnetic radiation produced by said Source (LS) of a beam of electromagnetic radiation reflects from an upper surface of said Sample (SS) and enters said detector of said beam of electromagnetic radiation, such that in use when the First Pivot Means (FPM) at which said First (FA) and Second (SA) arms are interconnected is caused to be vertically raised or lowered, the angle of incidence at which the Beam (E) of electric radiation approaches said sample surface is changed, but the location at which it interacts with said Sample (SS) surface remains substantially unchanged.

It is noted that designators (E), (EM), (EMB1), (EMB2) in the various Figures all identify a Beam of Electromagnetic Radiation from a Source (LS) thereof.

It is noted that Reflectometer, Spectrophotometer Ellipsometer, Polarimeter, Mueller Matrix Measuring System and the like systems can be generically termed "material system investigating systems".

It is also noted that it is within the scope of the invention to provide the angle-of-incidence changing system on only one side of a sample.

The terminology "focusing optics" is used in the Claims to indicate that any optics, lens or mirror, can be applied to focus and/or re-collimate an electromagnetic beam.

Finally, it is believed that the present invention is unique in many respects, but is definitely new, novel and non-obvious in teaching the use of focused beams which are caused to approach a sample along an oblique angle of incidence to align the vertical position of said sample in an ellipsometer or the like system, followed by removal of the focusing means prior to acquiring data. The present invention teaches that focusing an oblique angle of incidence beam onto a sample improves the sensitivity to the vertical positioning of said sample and allows more precise vertical positioning, but that it is not always preferable to then acquire data with the focusing means in place. The present invention provides for easily providing focusing, or not, of a beam at a single angle of incidence, at least one angle-of-incidence.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system comprising:
source of a beam of spectroscopic electromagnetic radiation;
stage for supporting a sample;
data detector of spectroscopic electromagnetic radiation;
said system further comprising, between said source and stage, means for receiving a beam of spectroscopic electromagnetic radiation from said source thereof and providing it to a surface of a sample on said stage at any of at least two angles-of-incidence with respect to said surface, with at least one of said angles-of-incidence being available as a focused, and as a non-focused, beam onto said sample surface;
said source of a beam of spectroscopic electromagnetic radiation, data detector of spectroscopic electromagnetic radiation, and means for receiving a beam of spectroscopic electromagnetic radiation from said source thereof and providing it to a surface of a sample on said stage at any of at least two angles-of-incidence with respect to said surface, being functionally mounted so as to enable movement as a unit;
said system further comprising means for detecting the direction in which a normal to a sample surface projects and means for detecting the angle and plane of incidence of a beam of electromagnetic radiation provided by said source of a beam of spectroscopic electromagnetic radiation, and providing signals which are representative thereof;
said system further comprising actuator means for receiving said representative signals and in response automatically controlling the separation between:
as a unit, said source, data detector, and means for receiving a beam of spectroscopic electromagnetic radiation from said source thereof and providing it to a sample on said stage; and
the surface of a sample on said stage;
said system further comprising actuator means for receiving said representative signals and in response automatically controlling the effective tip/tilt between said beam of electromagnetic radiation provided by said source of a beam of spectroscopic electromagnetic radiation with respect to said sample surface, and therefor the orientation of the angle and plane of incidence of said spectroscopic beam of electromagnetic radiation provided by said source of a beam of spectroscopic electromagnetic radiation with respect to said sample surface; and
optionally, means for causing rotation of said sample about a normal to said surface thereof.

2. A system as in claim 1, which further comprises between said stage and detector, means for receiving a beam of spectroscopic electromagnetic radiation reflected from said sample and providing it to said detector in any of at least two angles-of-incidence with respect to said surface, with at least one of said angles-of-incidence being available as a focused, and as a non-focused, beam onto said sample surface.

3. A system as in claim 1, which further comprises a polarizer between said source of a beam of spectroscopic electromagnetic radiation said stage, and an analyzer between said stage and said detector, and in which said system is an ellipsometer or polarimeter.

4. A system as in claim 1, in which actuator action causes a normal to the sample surface at the point at which said beam of spectroscopic electromagnetic radiation impinges, to project substantially vertically upward in laboratory coordinates.

5. A system comprising:
source of a beam of spectroscopic electromagnetic radiation;
stage for supporting a sample;
data detector of spectroscopic electromagnetic radiation;
said system further comprising, between said source and stage, means for receiving a beam of spectroscopic electromagnetic radiation from said source thereof and providing it to the surface of a sample on said stage at any of at least two angles-of-incidence with respect to said surface, with at least one of said angles-of-incidence being available as a focused, and as a non-focused, beam onto said sample surface;
said system being characterized by at least one selection from the group consisting of:
a) said stage for supporting said sample comprises means for moving said sample in two orthogonal directions in a plane substantially parallel to said sample surface and/or in a direction substantially perpendicular thereto; and
b) the presence of means for moving, as a group, said source;
data detector; and
means for receiving a beam of
spectroscopic electromagnetic radiation from said source thereof and providing it to a sample on said stage;
in two orthogonal directions in a plane substantially parallel to said sample surface and/or in a direction substantially perpendicular thereto;
said system further comprising:
means for controlling stage tip/tilt and therefor the orientation of the plane in which said sample surface is present; and
optional means for causing rotation of said sample.

6. A system as in claim 5, in which the stage for supporting a sample is comprised of two sections:
the first section being comprised of means for adjusting a sample location in two dimensions substantially parallel to the surface of said sample, and
the second section being comprised of means for moving the first section in a direction to place said first section closer to or further away from said source, data detector and said means for receiving a beam of spectroscopic electromagnetic radiation from said source thereof and providing it to a sample on said stage, and for adjusting tip/tilt of the surface of said sample;
such that in use the first section of said stage can be applied to position a spot on a surface of a sample placed on said stage in a plane which is parallel to that of a plane formed by the two dimensions in which said first section can cause movement, and the second section of said stage can be applied to orient said surface of a sample placed on the first section with respect to a beam of spectroscopic electromagnetic radiation provided by said source thereof via adjustment of the location of a surface of a sample along a direction generally perpendicular to said sample surface, and to control the tip/tilt orientation of the plane in which said first section of said stage causes movement of said sample, such that the plane in which the first section causes the surface of a sample to move with respect to an electromagnetic beam from said source thereof can orient the plane of incidence, which includes both a perpendicular to the sample surface and the locus of said spectroscopic electromagnetic, so that both project substantially perpendicular to the sample surface.

7. A system as in claim 5, which further comprises a polarizer between said source of electromagnetic radiation and said stage, and an analyzer between said stage and said data detector and in which said system is an ellipsometer or polarimeter.

8. A system as in claim 5, which further comprises means for providing an alignment beam of electromagnetic radiation provided by said source of a beam of spectroscopic electromagnetic radiation or an alternative source, and an alignment detector, said alignment detector being positioned to detect when said sample is oriented so that said alignment beam approaches said sample surface so that, at the point of reflection therefrom, it reflects directly back along its incident locus, the purpose being to enable align said sample surface in a known orientation.

9. A system as in claim 5, which further comprises a beam modulator which modulates at least one selection from the group consisting of:
    said spectroscopic electromagnetic beam; and
    said alignment beam;
to distinguish said at least one selection from external light, thereby enabling use in rooms illuminated by non-modulated light.

10. A system as in claim 5, which further comprises between said stage and detector, means for receiving a beam of spectroscopic electromagnetic radiation reflected from said sample and providing it to said detector in any of at least two angles-of-incidence with respect to said surface, with at least one of said angles-of-incidence being available as a focused, and as a non-focused, beam onto said sample surface.

11. A method of aligning a beam of electromagnetic radiation onto a sample surface comprising:
    a) causing a beam of electromagnetic radiation to impinge upon a sample surface at an oblique angle of incidence such that it reflects into a data detector, said reflected beam optionally passing through a central hole in a multiple element alignment detector or being partially reflected via beam splitter means onto a multiple element alignment detector;
    b) causing said sample to be tilted/tipped to realize a selection from the group consisting of:
        the data detector signal is maximized; and
        the signals from the multiple elements of a multiple element alignment detector through which said beam is caused to pass or is reflected onto are essentially equal;
    c) at the same oblique angle of incidence, placing focusing and recollimating lenses into the pathway of said electromagnetic beam before and after said sample, respectively, and causing said sample to be raised or lowered such that a selection from the group consisting of:
        the data detector signal is maximized; and
        the signals from the multiple elements of a multiple element detector through which said beam is caused to pass or is reflected onto are essentially equal.

12. A method as in claim 11, in which steps b and c are itteratively repeated a plurality of times at a selection from the group consisting of:
    the same location on the sample surface; and
    a plurality of locations on the sample surface; to improve alignment.

13. A method as in claim 11, wherein said system further comprises feedback/actuator means; said feedback means being applied to receive at least one signal from at least one selection from the group consisting of:
    said data detector; and
    said alignment detector;
and wherein said actuator means effects sample tilt/tip and/or sample raising or lowering in steps b and c by automatic response to said received at least one signal.

14. A method as in claim 11, which further comprises the step of:
    d) removing the focusing lenses from the pathway of said beam of electromagnetic radiation and acquiring sample describing data from said data detector.

15. A method as in claim 11, wherein electromagnetic radiation is entered to the data detector is via a fiber optic, thereby providing a relatively small target for the focused electromagnetic beam in step c.

16. A method as in claim 11, in which an alignment beam of electromagnetic radiation provided by a selection from the group consisting of:
    said source of a beam of spectroscopic electromagnetic radiation; and
    an alternative source a beam of electromagnetic radiation; and an alignment detector are present with said alignment detector being positioned to detect when said sample is oriented so that said alignment beam approaches said sample surface so that, at the point of reflection therefrom, it reflects directly back along its incident trajectory, the purpose being to enable orienting said sample surface in a known orientation.

17. A method as in claim 16 in which a beam modulator modulates at least one selection from the group consisting of:
    said spectroscopic electromagnetic beam; and
    said alignment beam;
to distinguish said at least one selection from external light, thereby enabling use in rooms illuminated by non-modulated light, in which the electromagnetic beam is modulated to distinguish it from external light, to enable use in lit rooms.

18. A method of aligning a beam of electromagnetic radiation onto a sample comprising:
    a) providing a system comprising:
        a source of a beam of spectroscopic electromagnetic radiation;
        a stage for supporting a sample;
        a data detector of spectroscopic electromagnetic radiation;
    said system further comprising, between said source and stage, means for receiving a beam of spectroscopic electromagnetic radiation from said source thereof and providing it to a surface of a sample on said stage at any of at least two oblique angles-of-incidence to said surface, with at least one of said oblique angles-of-incidence being available as a focused and as a non-focused beam onto said sample surface;
    said system being further characterized by at least one selection from the group consisting of:
        said stage for supporting said sample comprises means for moving said sample in two orthogonal directions in a plane parallel to said sample surface; and
        the presence of means for moving as a group, said source, data detector and means for receiving a beam of spectroscopic electromagnetic radiation from said source thereof and providing it to a sample on said stage, in two orthogonal directions in a plane substantially parallel to said sample surface;
    said system further comprising:
        means for changing the distance between the sample and, as a group, said source, data detector, and said means for receiving a beam of spectroscopic electromagnetic radiation from said source thereof along a loccus substantially perpendicular to a normal to said sample surface;

said system further comprising means for controlling stage tip/tilt and therefor the orientation of the plane in which said sample surface is present;

said system further comprising means for providing an alignment beam of electromagnetic radiation provided by a selection from the group consisting of:
  said source of a beam of spectroscopic electromagnetic radiation; and
  an alternative source a beam of electromagnetic radiation;

and an alignment detector, said alignment beam and alignment detector being oriented and positioned to detect when said sample is oriented with a normal to its surface projecting such that when said alignment beam approaches said sample surface, at the point of reflection therefrom, it reflects directly back upward along its incident trajectory; and said system optionally comprising a second alignment detector positioned and oriented to monitor spectroscopic electromagnetic radiation reflected from said sample surface at an oblique angle;

b) placing a sample on said stage and causing an alignment beam of electromagnetic radiation to impinge upon a sample at a substantially normal angle to a surface of said sample, such that it reflects from said sample surface into said alignment detector, and causing said stage to cause said sample surface to be tilted/tipped such that the signals from the alignment detector indicate that said alignment beam of electromagnetic radiation caused to impinge upon the surface of said sample reflects therefrom along a normal angle to said sample surface;

c) causing a beam of spectroscopic electromagnetic radiation to approach the surface of said sample at an oblique angle thereto, and placing focusing lenses before and after said sample into the pathway of said spectroscopic beam of electromagnetic radiation, then causing said sample and/or, as a group, said source, data detector, and said means for receiving a beam of spectroscopic electromagnetic radiation from said source thereof, and providing it to a sample on said stage, to be moved along a locus substantially perpendicular to a normal to said sample surface, such that a selection from the group consisting of:
  the data detector signal strength is maximized; and
  signals from said optional second alignment detector indicate that the reflected beam is directed to substantially maximize data detector signal strength.

19. A method as in claim 18, in which steps b and c are itteratively repeated a plurality of times at a selection from the group consisting of:
  the same location on the sample surface; and
  a plurality of locations on the sample surface;
to improve alignment of said spectroscopic electromagnetic beam.

20. A method as in claim 18, wherein effecting tilt/tip and changing the distance between the sample and as a group, said source, data detector, and said means for receiving a beam of spectroscopic electromagnetic radiation from said source thereof, and providing it to a sample on said stage, in steps b and c, respectively, are effected by automatic systems which utilize feedback from said data detector and/or optionally, said alignment detectors.

21. A method as in claim 18, which further comprises the step of:

d) removing the focusing lenses from the pathway of said beam of electromagnetic radiation and acquiring sample describing data from said data detector.

22. A method as in claim 18, wherein electromagnetic radiation is entered to the data detector is via a fiber optic, thereby providing a relatively small target for the focused electromagnetic beam in step c.

23. A method as in claim 18 in which there is a known relationship between the loci of said alignment and said beam of spectroscopic electromagnetic radiation from said source thereof which is provided to said surface of a sample on said stage.

24. A method as in claim 18 in which:
  said at least two oblique angles-of-incidence of said beam of spectroscopic electromagnetic radiation from said source thereof to said surface of said sample, of which at least one of said oblique angles-of-incidence is available as a focused and as a non-focused beam,
are made available sequentially.

25. A method of aligning a beam of electromagnetic radiation onto a sample comprising
  a) providing a system comprising:
    source of a beam of spectroscopic electromagnetic radiation;
    stage for supporting a sample;
    data detector of spectroscopic electromagnetic radiation;
    said system further comprising, between said source and stage, means for receiving a beam of spectroscopic electromagnetic radiation from said source thereof and providing it to the surface of a sample on said stage at any of at least two angles-of-incidence to said surface, with at least one of said angles-of-incidence being available as a focused and as a non-focused beam onto said sample surface;
    said system being characterized by at least one selection from the group consisting of:
      said stage for supporting said sample comprises means for moving said sample in two orthogonal directions in a plane parallel to said sample surface; and
      the presence of means for moving as a group, said source, data detector and means for receiving a beam of spectroscopic electromagnetic radiation from said source thereof and providing it to a sample on said stage, in two orthogonal directions in a plane substantially parallel to said sample surface;
      the presence of means for moving the sample in a direction to place it closer to or further away from said source, data detector, and said means for receiving a beam of spectroscopic electromagnetic radiation from said source thereof, and providing it to a sample on said stage;
    said system further comprising means for controlling stage tip/tilt and therefor the orientation of the plane in which said sample surface is present, and
    said system optionally further comprising means for causing rotation of said sample;
    said system further comprising means for providing an alignment beam of electromagnetic radiation provided by a selection from the group consisting of:
      said source of a beam of spectroscopic electromagnetic radiation; and
      an alternative source a beam of electromagnetic radiation;
  and an alignment detector, said alignment beam and detector being oriented and positioned to detect when said sample is oriented and with a normal to its surface projecting such that said alignment beam approaches said sample surface and, at the point of reflection therefrom, reflects directly back upward along its incident trajectory, there being a known relationship between the loci of said alignment and said beam of spectroscopic electromagnetic radiation;

b) placing a sample on said stage and causing an alignment beam of electromagnetic radiation to impinge upon a sample at a substantially normal angle to a surface of said sample, such that it reflects from said sample surface into said alignment detector, and causing said stage to cause said sample surface to be tilted/tipped such that the signals from the alignment detector indicate that said alignment beam of electromagnetic radiation caused to impinge upon the surface of said sample reflects therefrom along a normal angle to said sample surface;

c) causing a beam of spectroscopic electromagnetic radiation to approach the surface of said sample at an oblique angle thereto, and placing focusing lenses before and after said sample into the pathway of said spectroscopic beam of electromagnetic, and optionally placing and orienting a second alignment detector to monitor reflected spectroscopic electromagnetic radiation from said sample surface, then causing said sample to be moved along a locus substantially perpendicular to a normal to said sample surface, such that a selection from the group consisting of:

the data detector signal strength is maximized; and signals from said second alignment detector indicate that the reflected beam is directed to substantially maximize data detector signal strength.

26. A method as in claim 25, in which steps b and c are itteratively repeated a plurality of times at a selection from the group consisting of:

the same location on the sample surface; and a plurality of locations on the sample surface;

to improve alignment of said spectroscopic electromagnetic beam.

27. A method as in claim 25, wherein effecting tilt/tip and sample raising or lowering in steps b and c are effected by automatic systems which utilize feedback from said data detector and/or optionally, said alignment detectors.

28. A method as in claim 25, which further comprises the step of:

d) removing the focusing lenses from the pathway of said beam of electromagnetic radiation and acquiring sample describing data from said data detector.

29. A method as in claim 25, wherein electromagnetic radiation is entered to the data detector is via a fiber optic, thereby providing a relatively small target for the focused electromagnetic beam in step c.

* * * * *